(12) United States Patent
Furch et al.

(10) Patent No.: US 12,059,475 B2
(45) Date of Patent: Aug. 13, 2024

(54) TARGETED NANOCARRIERS FOR TARGETED DRUG DELIVERY OF GENE THERAPEUTICS

(71) Applicant: RODOS BIOTARGET GMBH, Hannover (DE)

(72) Inventors: Marcus Furch, Frankfurt (DE); Robert Gieseler, Werdohl (DE)

(73) Assignee: SOLMIC BIOTECH GMBH, Düsseldorf (DE)

( * ) Notice: Subject to any disclaimer, the term of this patent is extended or adjusted under 35 U.S.C. 154(b) by 0 days.

(21) Appl. No.: 15/570,229

(22) PCT Filed: Apr. 29, 2016

(86) PCT No.: PCT/EP2016/059699
§ 371 (c)(1),
(2) Date: Oct. 27, 2017

(87) PCT Pub. No.: WO2016/174250
PCT Pub. Date: Nov. 3, 2016

(65) Prior Publication Data
US 2018/0140717 A1    May 24, 2018

(30) Foreign Application Priority Data

Apr. 29, 2015  (EP) ..................................... 15165736
Jul. 29, 2015  (EP) ..................................... 15002246

(51) Int. Cl.
| | |
|---|---|
| A61K 47/69 | (2017.01) |
| A61K 9/127 | (2006.01) |
| A61K 31/7125 | (2006.01) |
| A61K 38/00 | (2006.01) |
| A61K 38/46 | (2006.01) |
| A61K 47/54 | (2017.01) |
| A61K 47/61 | (2017.01) |
| C12N 15/11 | (2006.01) |

(52) U.S. Cl.
CPC .......... *A61K 47/6913* (2017.08); *A61K 9/127* (2013.01); *A61K 31/7125* (2013.01); *A61K 38/00* (2013.01); *A61K 38/465* (2013.01); *A61K 47/549* (2017.08); *A61K 47/61* (2017.08); *A61K 47/6911* (2017.08); *C12N 15/111* (2013.01); *C12N 2310/14* (2013.01); *C12N 2310/16* (2013.01); *C12N 2310/20* (2017.05); *C12N 2320/32* (2013.01)

(58) Field of Classification Search
CPC .. A61K 31/7125; A61K 38/00; A61K 38/465; A61K 47/549; A61K 47/61; A61K 47/6911; A61K 47/6913; A61K 9/127; C12N 15/111; C12N 2310/14; C12N 2310/16; C12N 2310/20; C12N 2320/32
USPC .......................................................... 424/50
See application file for complete search history.

(56) References Cited

U.S. PATENT DOCUMENTS

2007/0292494 A1*  12/2007  Gieseler ................. A61P 37/02
                                                     424/450
2017/0152507 A1*  6/2017  Yin ....................... C12N 15/102

FOREIGN PATENT DOCUMENTS

| WO | 2005/092288 A1 | 10/2005 | |
|---|---|---|---|
| WO | 2005092288 | 10/2005 | |
| WO | 2011108955 | 9/2011 | |
| WO | WO-2011108955 A1 * | 9/2011 | ........... A61K 9/1271 |
| WO | WO-2015006747 A2 * | 1/2015 | ......... A61K 48/0066 |
| WO | 2016/04043 A1 | 1/2016 | |

OTHER PUBLICATIONS

Frenz et al. European Journal of Pharmaceutics and Biopharmaceutics, vol. 95, pp. 13-17. (Year: 2015).*
Unger et al. Journal of Controlled Release, vol. 160, No. 1, pp. 88-95. (Year: 2012).*
Yin et al. Nature Reviews Genetics, vol. 15, No. 8, pp. 541-555. (Year: 2014).*
Kawakami et al. Biochimica et Biophysica Acta 1524 (2000) 258-265. (Year: 2000).*
International Search Report for PCT/EP2016/059699, Completed by the European Patent Office on Aug. 2, 2016, 7 Pages.

(Continued)

*Primary Examiner* — Janet L Epps-Smith
(74) *Attorney, Agent, or Firm* — Brooks Kushman P.C.

(57) ABSTRACT

A targeted nanocarriers also termed nanomedicines and methods of preferentially, or actively, targeting and delivering a tool for gene transfer or genome editing (i.e., a plasmid or a restriction enzyme such as a zinc finger nuclease, a CRISPR/Cas system, or a TALEN) or a tool for gene silencing or post-transcriptional regulation of gene expression (i.e., a microRNA, a siRNA, a mRNA, an antisense oligonucleotide, or a sense oligonucleotide) to a range of mammalian cell species. Cell specific targeting is achieved by using nanocarriers featuring suitable targeting anchors having a targeting moiety that can be a carbohydrate, an antibody or an antibody fragment, a non-antibody protein derivative, an aptamer, a lipoprotein or a fragment thereof, a peptidoglycan, a lipopolysaccharide or a fragment thereof, or a CpG DNA. Such targeting anchors may or may not include a polymeric spacer like polyethylene glycol. The nanomedicines shall allow to therapeutically address a range of mammalian disease entities via various application routes. These indications include malignant diseases, autoimmune diseases, inherited disorders, metabolic disorders, or infectious diseases.

2 Claims, 2 Drawing Sheets
Specification includes a Sequence Listing.

(56) References Cited

OTHER PUBLICATIONS

European Search Report for European Application No. EP 15002246, Completed by the European Patent Office on Apr. 11, 2016, 7 Pages.
Hao Yin et al. Nature Reviews Genetics Jul. 15, 2014, vol. 15, No. 8, pp. 541-555, XP 055240438, "Non-Viral Vectors for Gene-based Therapy".
James et al. Molecular Therapy Apr. 2000, vol. 1, No. 4, pp. 339-346, "Nuclear-associated plasmid, but not cell-associated plasmid, is correlated with transgene expression in cultured mammalian cells".
Peer et al. Nature Nanotechnology Dec. 2007, vol. 2, pp. 751-760, "Nanocarrieres as an emerging playform for cancer therapy".
Allen, Drugs 1998, vol. 56, No. 5, pp. 747-756, "Liposomal Drug Formulations, Rationale for Development and What We Can Expect for the Future".
Immordino et al. International Journal of Nanomedicine 2006, vol. 1, No. 3, pp. 297-315, "Stealth liposomes: review of the basic science rationale and clinical applications, existing and potential".
Silva et al. Current Drug Metabolism Apr. 2015, vol. 16, pp. 3-16, "Nucleic acids delivery systems: A challenge for pharmaceutical Technologists".
Aaldering et al. RNA Biol. 2015, vol. 12, No. 4, pp. 412-425, "Smart Functional Nucleic Acid Chimeras: Enabling Tissue Specific RNA Targeting Therapy".
Marraffini et al. Nat Rev Genet Mar. 2010, vol. 11, No. 3, pp. 181-190, "CRISPR interference: RNA-directed adaptive immunity in bacteria and archaea".
Barrangou et al. Science 2007, vol. 315, pp. 1709-1712, "CRISPR provides acquired resistance against viruses in prokaryotes".
Mali et al. Nature Methods Oct. 2013, vol. 10, No. 10, pp. 957-963, "Cas9 as a versatile tool for engineering biology".
Esvelt et al. elife 2014, e03401, 21 Pages, "Concerning RNA-guided gene drives for the alteration of wild populations".
Boch, Nature Biotechnology Feb. 2011, vol. 29, No. 2, pp. 135-136, "TALEs of genome targeting ".
Carlson et al. Citation: Molecular Therapy-Nucleic Acids 2012, 1:e3, 4 Pages, "Targeting DNA with Fingers and TALENs".
Siomi et al. Nature Jan. 22, 2009, vol. 457, pp. 396-404, "On the road to reading the RNA interfence code".
Sullivan et al. Antisense Research and Development 1992, vol. 2, pp. 187-197, "Inhibition of Human Immunodeficiency Virus-1 Proliferation by Liposome-Encapsulated Sense DNA to the 5' TAT Splice Acceptor Site".
Rajeev et al. Chembiochem 2015, vol. 16, pp. 903-908, "Hepatocyte-Specific Delivery of siRNAs Conjugated to Novel Non-Nucleosidic Trivalent N-Acetylgalactosamine Elicts Robust Gene Silencing in Vivo".
Gieseler et al. Scandinavian Journal of Immunology 2004, vol. 59, pp. 415-424, "DC-SIGN-Specific Liposomal Targeting and Selective Intracellular Compound Delivery to Human Myeloid Dendritic Cells: Implications for HIV Disease".
Bailey et al. Biochimica et Biophysica Acta 2000, vol. 1468, pp. 239-252, "Efficient Encapsulation of DNA plasmids in small neutral liposomes Inducediby ethanol and calcium".
Mbonye et al. Virology 2014, 454-455 : 328-339, "Transcriptional control of HIV latency: Cellular signaling pathways, epigenetics, happenstance and the hope for a cure".
Bechmann et al. Hepatol Res Jun. 2009, vol. 39, No. 6, pp. 601-608, "Resveratrol amplifies profibrogenic effects of free fatty acids on human hepatic stellate cells".
Cohen et al. Gene Therapy 2000, vol. 7, pp. 1896-1905, "Sustained delivery and expression of DNA encapsulated in polymeric nanoparticles".
Gieseler et al. J. Viral Hepat Nov. 2011, vol. 18, No. 11, pp. 760-767, "Hepatocyte apoptotic bodies encasing honstructural HCV proteins amplify hepatic stellate cell activation: implications for chronic hepatitis C".
Grunwald et al. Clinical Experimental Vaccine Research 2015, vol. 4, pp. 1-10, "Improvement of DNA vaccination by adjuvants and sophisticated delivery devices: vaccine-platforms for the battle against infectious diseases".
Hoving et al. Cellular Microbiology 2014, vol. 16, No. 2, pp. 185-194, "Signalling C-type lectin receptors, microbial recognition and ummunity".
Marraffini et al. Science Dec. 19, 2008, vol. 322, No. 5909, pp. 1843-1845, "CRISPR Interference Limits Horizontal Gene Transfer in Staphylococci by Targeting DNA".
Mocellin et al. Journal of Translational Medicine Nov. 2014, 6 Pages, "RNA interference: learning gene knock-down from cell physiology".
Courtney et al. International Journal of Ophthalmology and Eye Science Aug. 27, 2015, vol. s2, pp. 7-18, XP 055262988, "A review of Personalised Molecular Medicine for the treatment of Corneal Disorders".
Adijanto et al. European Journal of Pharmaceutics and Biopharmaceutics Jan. 12, 2015, 15 Pages, "Nanoparticle-based technologies for retinal gene therapy".
Ain et al. Journal of Controlled Release May 10, 2015, vol. 205, 15 Pages, "Current and future delivery systems for engineered nucleases: ZFN, TALEN and RGEN".
Arya et al. Science Jul. 5, 1985, vol. 229, Issue No. 4708, pp. 69-73, "Trans-activator gene of human T-lymphotropic virus type III (HTLV-III)".
Asprer et al. Stem Cell Reviews and Reports, Published Online Dec. 11, 2014, 16 Pages, "Current Methods and Challenges in the Comprehensive Characterization of Human Pluripotent Stem Cells".
Balbino et al. Langmuir 2012, vol. 28, pp. 11535-11545, "Correlation of the Physicochemical and structural properties of pDNA/cationic liposome complexes with their in vitro transfection".
Bertino et al. Biomed Res Int 2015; 2015: 731469, Epub 2015 Mach 29, Received Mar. 16, 2016; Accepted Mar. 16, 2016, "Retracted: The immune system in hepatocellular carcinoma and potential new immunotherapeutic strategies".
Birchall et al. International Journal of Pharmaceutics Jun. 25, 1999, vol. 183, Issue No. 2, pp. 195-207, "Physico-chemical characterisation and transfection efficiency of lipid-based gene delivery complexes".
Felgner et al. Nature Jan. 26, 1989, vol. 337, pp. 387-388, "Cationic liposome-mediated transfection".
Frankel et al. Cell 1988, vol. 55, pp. 1189-1193, "Cellular Uptake of theTat Protein from Human Immunodeficiency Virus".
Frenz et al. European Journal of Pharmaceutics and Biopharmaceutics Feb. 19, 2015, vol. 95, pp. 13-17, XP 029282582, "Atigen Presenting Cell-Selective Drug Delivery by Glycan-decorated Nanocarriers".
Gao et al. Bioconjugate Chem. 2010, vol. 21, pp. 604-609, "In Vivo Tumor-Targeted Fluorescence Imaging Using Near-Infrared Non-Cadmium Quantum Dots".
Green et al. Cell Dec. 23, 1988, vol. 55, No. 6, pp. 1179-1188, "Autonomous Functional Domains of Chemically Synthesized Human immunodeficiency Virus Tat Trans-Activator Protein".
Breous et al. Clinical Application of Basic Science, Journal of Hepatology 2011, vol. 54, pp. 830-834, "Potential of Immunotherapy for hepatocellular carcinoma".
Jabalameli et al. Received date, May 25, 2014, Revised date, Dec. 9, 2014, Accepted date, Dec. 19, 2014, 18 Pages, "Zinc Finger Nuclease Technology: Advances and Obstacles in Modelling and Treating Genetic Disorders".
Kessler et al. Gene 1990, vol. 92, pp. 1-248, "Specificity of restriction endonucleases and DNA modification Mythyltransferases: A review (Edition 3)".
Wang et al. Annu. Rev. Med 2012, vol. 63, pp. 185-198, "Nanoparticles Delivery of Cancer Drugs".
Wree et al. Nature Reviews Gastroenterology and Hepatology Nov. 2013, vol. 10, 10 Pages, "From NAFLD to NASH to cirrhosis—new insights into disease mechanisms".
Li et al. Human Gene Therapy Jun. 2, 2015, vol. 26, No. 7, pp. 452-462, XP 055263140, "Challenges in CRISPR/CAS9 Delivery: Potential Roles of Nonviral Vectors".

(56) References Cited

OTHER PUBLICATIONS

Perez-Herrero et al. European Journal of Pharmaceutics and Biopharmaceutics Mar. 23, 2015, 28 Pages, "Advanced targeted therapies in cancer: Drug nanocariiers, the future of chemotherapy".
Perrie et al. Vaccine 2001, vol. 19, pp. 3301-3310, "Liposome-mediated DNA vaccination: the effect of vesicle composition".
Pupo et al. Journal of Controlled Release May 18, 2005, vol. 104, Issue No. 2, pp. 379-396, "Preparation of plasmid DNA-containing lipsomes using a high-pressure homogenization-Extrusion technique".
Sarvaiya et al. International Journal of Biological Macromolecules 2014, vol. 72, 12 Pages, "Chitosan as a suitable nanocarrier material for anti-Alzheimer drug delivery".
Seog-Jin et al. Nanomedicine Nov. 2013, vol. 8, No. 11, pp. 1875-1891, XP 055262988, "Gene Delivery Techniques for Adult Stem cell-based Regenerative Therapy".
Tachibana et al. Pharmsvrutical Research Apr. 2002, vol. 19, Issue No. 4, pp. 377-381, "Quantitative analysis of correlation between number of nuclear plasmids and gene expression activity after transfection with cationic ipsomoes".
Unger et al. Journal of Controlled Release Feb. 9, 2012, vol. 160, No. 1, pp. 88-95, XP 028507666, "Glycan-modified Liposomes Boost CD4and CD8T-cell responses by targeting DC-SIGN on Dendritic Cells".
Xenopoulos et al. Expert Reviews Vaccines 2014, vol. 13, No. 12, pp. 1537-1551, "Production and purification of plasmid DNA vaccines: in there scope for further innovation?".
Yao et al. Human Gene Therapy Jun. 12, 2015, vol. 26, No. 7, pp. 463-471, XP055262993, "CRISPR/Cas9-Mediated Genome Editing of Epigenetic Factors for Cancer Therapy".
Klug et al. Cold Spring Hard Symp Quant Biol 1987, vol. 52, Biliographic Data, 3 Pages, "Zince Fingers: A novel protein fold for nucleic acid recognition".
Goodchild J. Chapter I. Therapeutic Oligonucleotides. In: Goodchild J. (ed.). Methods in Molecular Biology: Therapeutic Oligonucleotides. Methods and Protocols. Springer 2011: ISBN 978-1-61779-188-8, Bibliographic Data with Abstract all together 2 Pages.
Roberts , CRC Crit. Rev. Biochem 1976, vol. 4, Abstract and bibliographic Data All together 2 Pages, PMID 795607, "Restriction endonucleases".
Sharma, Curr. Drug Targets 2014, vol. 15, Abstract and Bibliographic Data, All together 3 Pages , PMID 25174340, "Nanotheranostics in evidence based personalized medicine".
Ulrich et al. Journal of Medical Virology May 1988, vol. 25, No. 1, Abstract and Bibliographic Data, All together 3 Pages, "Assessment of human immunodeficiency virus expression in cocultures of peripheral blood mononuclear cells from healthy seropostive subjects".
Website Gene Silencing NCIB http://www.ncib.nlm.nih.gov/probe/doc/applsilencing/ Retrieved from the Wayback Machine Mar. 21, 2018, Website Dated Feb. 19, 2015, All together 4 Pages, "Gene silencing-interruption or suppression of the expression of a gene at transcriptional or translational levels".
Rozema, D.B. et al., "Dynamic PolyConjugates for targeted in vivo delivery of siRNA to hepatocytes," PNAS, Aug. 7, 2007, v. 104, n. 32, pp. 12982-12987.
Lu, B., "New Techniques and New Dosage Forms of Drugs," People's Health Publishing House, 2005, 8 pgs.
Kan, Q., "Advanced Course of Hospital Pharmacy," People's Military Medical Press, 2015, 6 pgs.
Givens, B.E. et al., "Nanoparticle based delivery of CRISPR/Cas9 genome editig therapeutics," AAPS J.; 20(6), 108, 2019, pp. 1-37.
Solaro, R. et al., "Targeted Delivery of Protein Drugs by Nanocarriers," Materials 2010, v. 3, pp. 1928-1980.
Thapa, B. et al., "Lipoplex," https://www.sciencedirect.com/topics/neuroscience/lipoplex, downloaded Jul. 16, 2021, 12 pgs.

* cited by examiner

SEQUENCE LISTING

```
<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: sense sequence of the synthetic oligonucleotide

<400> SEQUENCE: 1
attttcagaa ttgggtgtcg                                                  20
```

TARGETED NANOCARRIERS FOR TARGETED DRUG DELIVERY OF GENE THERAPEUTICS

CROSS-REFERENCE TO RELATED APPLICATION

This application is the U.S. national phase of PCT Application No. PCT/EP2016/059699 filed on Apr. 29, 2016, which claims priority to EP Patent Application No. 15165736.8 filed on Apr. 29, 2015, and EP Patent Application No. 15002246.5 filed on Jul. 29, 2015, the disclosures of which are incorporated in their entirety by reference herein.

SEQUENCE LISTING

The text file Sequence_Listings_PCT_EP2016_059699.TXT of size 1 KB created Oct. 25, 2017, filed herewith, is hereby incorporated by reference.

FIELD OF THE INVENTION

The present invention relates to the medical arts and in particular to the targeted delivery of gene-therapeutic agents by nanocarriers to mammalian cells affected by a range of disease entities that may be treated or cured by such therapeutic intervention.

BACKGROUND OF THE INVENTION

A number of hurdles continue to challenge targeted delivery of bioactive molecules to mammalian cells (e.g., cancer cells), particularly in-vivo. Those hurdles include (a) the composition, functional characteristics and stability of delivery vehicles, (b) packaging therapeutically significant concentrations of bioactive molecules, (c) targeting desired diseased cells in-vivo, (d) overcoming various intracellular barriers and successfully delivering therapeutic concentrations of bioactive molecules to intracellular targets, (e) avoiding a range of components of the host's immune system such as antibodies, complement factors and macrophages that may destroy a delivery vehicle before it reaches its target, (f) crossing the endothelial barrier of blood vessel walls, particularly at the site of a tumor mass, (g) migrating through several layers of cells to reach a target (e.g., it is known that a solid tumor is an organized structure containing both tumor cells and normal cells; hence a delivery vehicle must cross several layers of normal cells to access malignant cells), (h) migrating through an extracellular matrix (ECM) comprised of glycoproteins, sulfated glycosaminoglycans, hyaluronan, proteoglycans and collagen that fills the space between cells and therefore hampers the traffic of a delivery system, and (i) addressing high interstitial hypertension (i.e., elevated hydrostatic pressure outside blood vessels) in the cell's microenvironment, which may limit the access of bioactive molecules to their site of action.

A number of different delivery vehicles have been proposed for both nucleic acid and drug delivery, including viral, non-viral non-living, and non-viral living vehicles. The non-viral non-living vehicles have been adapted for both nucleic acid and drug delivery. The other two types of vehicles have been mostly adapted for nucleic acid delivery. All these vehicles have advantages and drawbacks alike.

Non-viral non-living vehicles (vectors) are exemplified by cationic polymers (polyplexes), cationic lipids (liposomes, lipoplexes) and synthetic nanoparticles (nanoplexes). They are more versatile than viral vectors and offer several distinct advantages because their molecular composition can be controlled, manufacturing and analysis of such vectors is fairly simple, they can accommodate a range of transgene sizes and they are less immunogenic The efficiency of gene delivery with non-viral non-living vectors is significantly less, however, than with viral vectors. At least $10^6$ plasmid copies are needed to transfect a single cell, with approximately $10^2$-$10^4$ copies actually making it to the nucleus for transgene expression (Felgner et al., 1989; James et al., 2000; Tachibana et al., 2002). This inefficiency is attributable to the inability of non-viral non-living vector to overcome the numerous challenges encountered between a site of administration and localization in a target cell's nucleus, including, (a) the physical and chemical stability of DNA and its delivery vehicle in the extracellular space, (b) cellular uptake by endocytosis, (c) escape from the endosomal compartments prior to trafficking to lysosomes and cytosolic transport, and (d) nuclear localization of the plasmid for transcription.

The development of nanotechnology brought the promise to revolutionize many fields in science by introducing the possibility to manipulate different materials at the nanoscale size rendering a variety of structures with different applications in areas such as cell-based therapies or diagnosis. Nanocarriers represent one of the byproducts that emerged from nanotechnology research. Numerous nanoparticles have been developed, including carbon nanotubes, polymeric carriers, dendrimers, metal particles (e.g. gold nanoshells) and lipid-based particles (e.g. liposomes) (Peer D et al. Nat Nanotech 2007; 2:751-60). Of all mentioned particles, liposomes are currently one of the most advanced systems for drug delivery with several formulations approved for clinical use (Wang A Z et al. Annu Rev Med 2012; 63:185-98).

Liposomes are vesicular organized structures, i.e. phospholipid membrane bilayers surrounding an inner aqueous core (Allen, 1998). The success of these systems is due to their biocompatible and biodegradable composition, which further enables to encapsulate hydrophilic agents in the inner aqueous core, hydrophobic drugs in the membrane bilayer or amphiphilic agents in both compartments, thus protecting them from degradation (Allen T M. Drugs 1998; 56:747-56; Wang A Z et al. Annu Rev Med 2012; 63:185-98). Additionally, liposomes modify the pharmacokinetic and biodistribution profiles of the encapsulated drugs (Allen T M. Drugs 1998; 56:747-56).

The "first generation" of liposomal formulations presented a rapid blood clearance, along with accumulation within the mononuclear phagocyte system (MPS), following opsonization (Immordino M L et al. Int J Nanomedicine 2006; 1:297-315; Wang A Z et al. Annu Rev Med 2012; 63:185-98). Long-circulating liposomes emerged afterwards as a "second generation", by modulation of lipid composition and, especially, by the incorporation of poly-(ethyleneglycol)—"PEG"—onto the liposomal surface. PEG creates a "hydrophilic cloud" around the particle, thus minimizing the opsonization process and clearance by the MPS, rendering a technology known as Stealth® liposomes (Immordino M L et al. Int J Nanomedicine 2006; 1:297-315). The same strategy has been applied to other particles in order to increase their blood circulation times. However, passive targeting does not address the issue of specific drug delivery. In order to circumvent this limitation, one can actually further modify the nanoparticle surface with internalizing targeting moieties (Peer D. et al. Nat Nanotech 2007; 2:751-60; Wang A Z et al. Annu Rev Med 2012; 63:185-98). Several targeting moieties have been used, including antibodies, Fab' and F(ab')$_2$ fragments, aptamers, small peptides or nanobodies, among others, which recognize (over)expressed receptors at the cell surface and promote active internalization of the nanoparticles (Peer D et al. Nat Nanotech 2007; 2:751-60). For example, Gao et al. used RGD peptide to promote targeted delivery of quantum dots for tumor fluorescence imaging (Gao J et al. Bioconj Chem 2010; 21:604-9). Despite increasing the drug accumulation into the target cell (in-vitro), intracellular delivery does not necessarily guarantee increased bioavailability, as the drug (functionally active) has to escape from the endosomal compartment.

Cancers are a major example for targeted treatments. Ranking only second to cardiovascular diseases, cancers are the second worldwide cause of death. Besides other treatment options, malignancies are treated by chemotherapy. However, these aggressive agents also affect rapidly proliferating healthy bystander cells. Thus, the toxicity and the development of multidrug resistance against chemotherapeutic drugs call for safe and effective targeted treatments. Pérez-Herrero and Fernández-Medarde recently reviewed that such targeted strategies allow to specifically deliver the chemotherapeutic agents to tumors, to avoid normal healthy tissues, to reduce systemic toxicity, to protect the drugs from degradation, and to increase their half-life, solubility as well as to reduce renal clearance. To date, two polymer-protein conjugates, five liposomal formulations and one polymeric nanoparticle are already available in the marketplace. However, due to the many advantages these new targeted treatments, there are numerous clinical trials in progress (Pérez-Herrero E and Fernández-Medarde A. Eur J Pharm Biopharm 2015 Mar. 23). Improvements in 'classical' cancer treatments allow for only modest impacts on patient survival.

Until now the cell-targeted delivery of nucleic acids is a challenge. This is mostly due to inefficient delivery of the nucleic acids into cells and nuclei which, in fact, is a topic for targeted drug delivery Grunwald and Ulbert recently discussed technologies used to overcome this problem by physical means such as in-vivo electroporation and co-administration of adjuvants (Grunwald T and Ulbert S. Clin Exp Vaccine Res 2015). Other efforts for improvement build upon upgrading methods for the production and purification of plasmid DNA (Xenopoulos A and Pattnaik P. Expert Rev Vaccines 2014; 13:1537-51). Various strategies have also been developed that can be implemented into plasmid DNA so as to generate persistent, high levels of gene expression (Adijanto J and Naash M I. Eur J Pharm Biopharm 2015 Jan. 12).

As already mentioned above, nucleic acids are not very efficient when administered in free form. Thus, their successful application for treating diseases requires to employ nanocarriers that allow the therapeutic nucleic acids to safely and efficiently enter cells (Silva A C et al. Curr Drug Metab 2015 Apr. 1). This need was recently epitomized by Aaldering and colleagues by stating: "A major obstacle for effective utilization of therapeutic oligonucleotides such as siRNA, antisense, antimiRs etc. is to deliver them specifically to the target tissues. Poor cellular uptake of therapeutic oligonucleotides impedes gene-targeting efficacy in-vitro and in-vivo." (Aaldering L J et al. RNA Biol 2015; 12:412-25).

SUMMARY OF THE INVENTION

Since problems continue to hamper the success of therapeutics, an urgent need exists for targeted delivery strategies that will either selectively deliver bioactive agents to target cells and target organs, or protect normal tissues from administered therapeutic agents. Such strategies should improve the efficacy of treatment by increasing the therapeutic indexes of therapeutic agents, while minimizing the risks of therapy-related toxicity.

Thus, the objective of the present invention is to provide a method for delivering an active agent specifically to a specific cell species in order to treat several diseases in a mammal.

This object has been solved by the subject-matter of claim 1. Preferred embodiments are defined in the dependent claims.

Thus, the present invention relates to a method of preferentially delivering a drug to a cell species of a mammalian subject by using a nanocarrier comprising a targeting anchor specific for a given cell species to therapeutically address a mammalian disease entity, wherein the drug is a gene-therapeutic tool for genome editing, genome silencing or the post-transcriptional regulation of gene expression, said tool being selected from a plasmid, an artificially engineered restriction enzyme, a plasmid specifically encoding a meganuclease, or a tool for transcriptional or post-transcriptional gene regulation.

Generally, the present invention relates to targeted nanocarriers—also termed nanomedicines—and methods of preferentially, or actively, targeting and delivering a tool for gene transfer or genome editing (i.e., a plasmid or a restriction enzyme—such as a zinc finger nuclease, a CRISPR/Cas system, or a TALEN) or a tool for gene silencing or post-transcriptional regulation of gene expression (i.e., a microRNA, a siRNA, a mRNA, an antisense oligonucleotide, or a sense oligonucleotide) to a range of mammalian cell species. Cell-specific targeting is achieved by using nanocarriers featuring suitable targeting anchors having a targeting moiety that can be a carbohydrate, an antibody or an antibody fragment, a non-antibody protein derivative, an aptamer, a lipoprotein or a fragment thereof, a peptidoglycan, a lipopolysaccharide or a fragment thereof, or a CpG DNA. Such targeting anchors may or may not include a polymeric spacer like polyethylene glycol. The nanomedicines shall allow to therapeutically address a range of mammalian disease entities via various application routes. These indications include malignant diseases, autoimmune diseases, inherited disorders, metabolic disorders, or infectious diseases.

In a preferred embodiment, the present invention relates to hepatocyte-specific nanocarriers encapsulating either mRNA or DNA for translation or expression in hepatocytes, respectively.

DETAILED DESCRIPTION OF THE PREFERRED EMBODIMENTS

Figure 1:
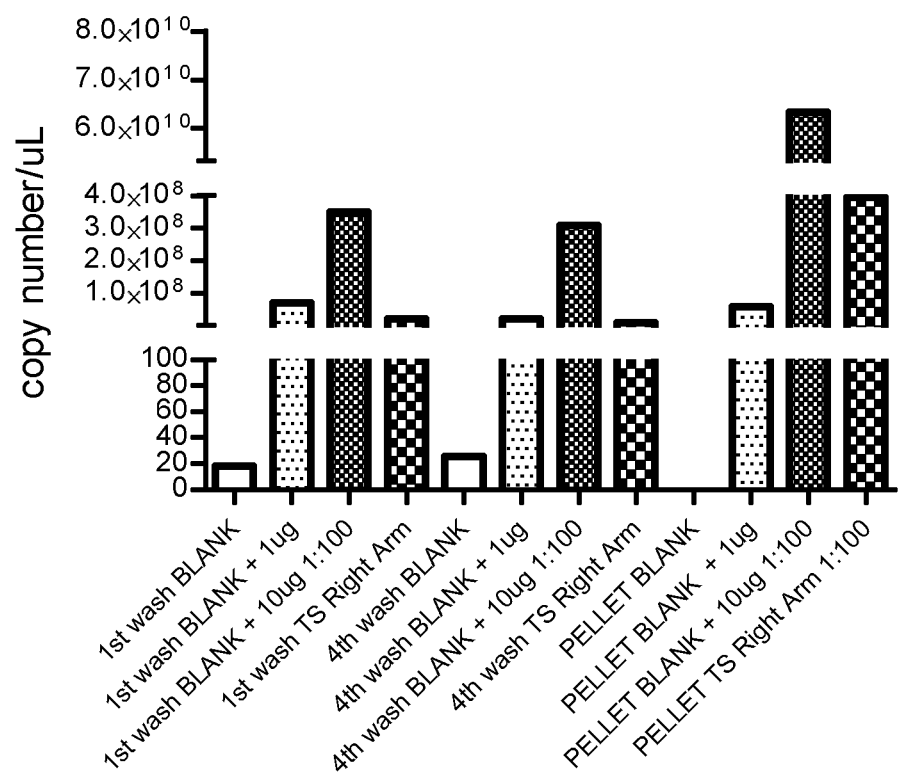
FIG. 1: Q-PCR demonstrated highly acceptable DNA encapsulation rates (copy number per μL) depending on the purification steps.

Some embodiments of the present invention are directed to a method of preferentially delivering an active agent or drug to cells of a mammalian subject, including a human that expresses surface receptors enabling receptor-mediated uptake of a targeted nanocarrier so as to deliver its therapeutic payload into said cell. The classes and types of cells are specified below.

The term "preferentially" means that the targeted nanocarrier is delivered to a cell of a mammalian subject, including a human expressing the targeted structure, and that the gene-therapeutic active agent associated with the targeted nanocarrier is taken up by said cell more effectively than the same active agent (i) in its freely soluble form or (ii) when associated with a comparable nanocarrier having an outer surface that does not comprise the targeting ligand.

The "method" involves injecting into the mammalian subject, including a human, a targeted nanocarrier in accordance with the invention that comprises the gene-therapeutic active agent as well as the targeted cell species affected by a malignant disease, an autoimmune disease, an inherited disorder, a metabolic disorder, or an infectious disease. In the special case that the targeted cell species is a stem cell, the gene-therapeutic active agent will not address a diseased cell but a cell that is utilized for regenerative therapeutic purposes. The targeted cell species are defined further below.

The term "active agent" or "drug" means a gene-therapeutic tool for either genome editing, genome silencing or the post-transcriptional regulation of gene expression. In a preferred embodiment, said tool is selected from a plasmid, an artificially engineered restriction enzyme, a plasmid specifically encoding a meganuclease, or a tool for transcriptional or post-transcriptional gene regulation. In a preferred embodiment, the artificially engineered restriction enzyme belongs to the group of meganucleases, e.g. is a zinc finger nuclease (ZFN), a CRISPR/Cas system or a transcription activator-like effector nuclease (TALEN). In a preferred embodiment, the tool for transcriptional or post-transcriptional gene regulation is a siRNA, a micro-RNA, a mRNA, an antisense oligonucleotide, or a sense oligonucleotide. In a further preferred embodiment, the plasmid expresses a gene either upon integration into the host cell genome or extra-chromosomally, hence leading to the translation of a peptide or protein gene product. In a preferred embodiment, the artificially engineered restriction enzyme or the tool for transcriptional or post-transcriptional gene regulation can be co-encapsulated with cell-penetrating peptides (CPPs), which include endosomal escape peptides. By definition, CPPs allow to cross a cellular membrane. A selection of which includes classical CPPs (Tat[48-60], penetratin (Antp[43-58]), transportan, TP10, Oligoarginine (R8), MAP, MPG, MPGα) and new CPPs (hCT[9-32]-br, SAP, S4[13]-PV, mPrPp, bPrPp, M918, EB1 and various CPP5s).

In a preferred embodiment, the present invention relates to a hepatocyte-targeted formulation for translation in hepatocytes. In another preferred embodiment, the present invention relates to a hepatocyte-targeted formulation for hepatocellular expression.

In a preferred embodiment the cell species is selected from the group consisting of a stem cell, a myeloid antigen-presenting cell, a non-myeloid antigen-presenting cell, a T lymphocyte, a B lymphocyte, a natural killer (NK) cell of the innate immune system, a glial cell, a liver cell, a pneumocyte, a myocyte, a neuron, a keratinocyte, a fibroblast, a chondrocyte, an exocrine glandular cell, an endocrine glandular cell, an endothelial cell, an epithelial cell, or a malignant cell resulting from the malign degeneration of healthy stem cells or somatic cells.

In a preferred embodiment the nanocarrier is a lipid-based nanocarrier, preferably a liposome, a lipoplex, or a micelle.

In another preferred embodiment the nanocarrier is not based on lipids, preferably the non-lipid-based nanocarrier is a synthetic polymeric nanoparticle, a dendrimer, a carbon nanotube, or a colloidal gold nanoparticle. It is particularly preferred that the synthetic polymeric nanoparticle is a poly(D,L-lactic-co-glycolic acid) nanoparticle. It is also particularly preferred that the colloidal gold nanoparticle is a gold nanoshell or a gold nanocage.

In another preferred embodiment of the present invention, the nanocarriers are chosen as to their cationic charge, wherein strongly or weakly cationic nanocarriers may be selected, preferably strongly cationic nanocarriers. The latter are preferably composed of, e.g., 1,2-dioleoyl-3-trimethyl-ammonium propane (DOTAP) and cholesterol, more preferably composed of, e.g., 53 mol % DOTAP and 39 mol % cholesterol, with the residual 8 mol % representing the targeting ligand; the latter preferably comprises lower mol-percentages of DOTAP and cholesterol, plus a neutral membrane phospholipid.

In a preferred embodiment the targeting anchor comprises a lipid anchor moiety and a targeting moiety which may be a carbohydrate residue, an antibody or an antibody fragment, a non-antibody protein, an aptamer, a lipoprotein or a fragment thereof, a peptidoglycan, a lipopolysaccharide or a fragment thereof, or a CpG DNA. Preferably, the carbohydrate residue is based on a monovalent or multivalent, linear or branched fucose or galactose or N-acetylgalactosamine (GalNAc), or on the natural polysaccharide chitosan.

In a preferred embodiment a spacer moiety is inserted between the lipid anchor moiety and the targeting moiety, particularly wherein the spacer moiety is 3,4,5-trihydroxy-6-(hydroxymethyl)tetrahydro-2H-pyran-2-yl)thioureido) butyl)carbamate, N-hydroxysuccinimide (NHS), 1,2-Distearoyl-sn-glycero-3-phosphoethanolamin-N-[poly (ethyleneglycol)-2000]-N-hydroxysuccinimid (DSPE-PEG-NHS), ε-aminocaproic acid, a polyaldehyde, a polyolefin, a polyethylene oxide, a poly-ω-alkenoic acid ester or a polyalkyl methacrylate.

In further preferred embodiment the targeting anchor is Gal-C4-Chol or GalNAc.

In a preferred embodiment the targeting anchor is directly linked to the nanocarrier but it may also linked thereto via a spacer. Such a spacer moiety is preferably additionally equipped with a polyethylene glycol moiety or a hydroxyethyl starch moiety.

According to the present invention, the targeting anchor specifically binds to a receptor molecule expressed on the surface of the cell species via the targeting moiety. Examples of receptor molecules are
- a C-type lectin or a non-C-type lectin;
- a Toll-like receptor (TLR) if the targeting moiety is a lipoprotein, peptidoglycan, lipopolysaccharide or CpG DNA, wherein the TLR is preferably TLR-1, TLR-2, TLR-4, TLR-6 or TLR-9;
- a marker on the surface of the cell species,
- a disease-related marker on the surface of the cell species; or.
- CD20, CD30, CD33, CD52, CEA, EGFR/ErbB1, HER2/ErbB2, c-MET/HGFR, IGFR1, EphA3, TRAIL-R1, TRAIL-R2, RANKL, VEGFR, $\alpha V\beta 3$, or $\alpha 5\beta 1$.

In a preferred embodiment, the mammalian disease entity is a malignant disease, an autoimmune disease, an inherited disorder, a metabolic disorder, or an infectious disease. The infectious disease may be caused by an infectious agent being selected from a virus, a bacterium, a fungus, or a protozoan.

In a preferred embodiment the mode of delivery of the nanocarrier is via an intravenous, a subcutaneous, an intradermal, an intraperitoneal, a parenteral, or an intrapulmonary route, a route by infusion via the hepatic artery, an intrathyroidal route, an intranasal route for pulmonary delivery, an intranasal route for nose-to-brain delivery, an intrathecal route, an application to the posterior segment of the eye, an intravitreal or a topical route, or a route by direct cellular treatment ex vivo before re-inoculation into a patient.

According to a preferred embodiment of the present invention the nanocarriers can be equipped with any of the above mentioned targeting anchors, with or without spacers, so as to generate a most versatile nanocarrier platform. In this regard any two to three nanocarriers having identical targeting moieties but loaded with different gene-therapeutic tools can employed synchronously if required for achieving the best possible therapeutic result for a patient.

Tools for Gene Transfer or Genome Editing

The term "plasmids" means small cellular DNA molecules that can replicate independently from their chromosomal DNA and that occur in bacteria, archaea and eukaryotic organisms. Artificial plasmids are employed as vectors in molecular cloning where they allow for replicating recombinant DNA within a host organism. The size of plasmids ranges between approx. 1 to 1,000 kbp and may be used as active agents according to the present invention. Apart from their multiple natural functions, plasmids may be used for in gene therapy (i) for expressing a protein for vaccination purposes within human or animal host cells or (ii) by transferring a functional gene into human or animal cells so as to express the functional protein that is lacking in a given disease. To this end, the therapeutic gene may have to be inserted at a pre-selected chromosomal target sites within the human genome or be transcribed extrachromosomally. If applying a plasmid vector for introducing the functional gene, a zinc finger nuclease may be preferably used to allow for this homologous recombination. According to the present invention, this may even be enabled by plasmids encoding the zinc finger nuclease itself. Plasmid-encoded DNA vaccines have so far shown most efficient immunogenicity in small rodent models, but there is there is still a need to improve effectiveness in humans and larger animals. This is mostly due to inefficient delivery of the DNA plasmid into cells and nuclei which, in fact, is a topic for targeted drug delivery according to the method of the present invention. However, the generally inefficient delivery of plasmids—such as for non-encapsulated nucleic acids in general—into cells clearly is a topic for targeted drug delivery according to the present invention.

Cells can protect themselves from genetics attacks from viruses, fungi and bacteria by 'molecular scissors' (restriction enzymes) that in a targeted manner cut the genetic information from a foreign organism into pieces before it can damage the host cell. Such "restriction enzymes" or "restriction endonucleases" cut DNA strands at a specific sequence at or near specific recognition nucleotide sequences known as restriction sites. These restriction sites in the foreign genome are usually four to six base pairs long. The DNA is cut by two incisions through the sugar-phosphate backbone of the DNA double helix (Roberts R J. Restriction endonucleases. CRC Crit Rev Biochem 1976; 4:123-64; Kessler C and Manta V. Gene 1990; 92:1-248). According to the present invention, restriction enzymes of different kinds can be brought into cell species by the claimed method and used as tools for gene therapeutic purposes.

The term "meganucleases" means endodesoxyribonucleases characterized by a large recognition site (double-stranded DNA sequences of 12 to 40 bp) which generally occurs only once in any given genome. Meganucleases are therefore considered to be the most specific naturally occurring restriction enzymes. The high specificity of meganucleases gives them a high degree of precision and much lower toxicity than other naturally occurring restriction enzymes. Examples of meganucleases are homing endonucleases from the LAGLIDADG family. Also ZFNs, CRISP/Cas, and TALEN are jointly referred to the emerging drug class of meganucleases.

Zinc finger nucleases (ZFNs) are artificially engineered restriction enzymes designed to target specific DNA sequences within the genome. A zinc finger is a small protein structural motif that is stabilized by zinc ions. Zinc fingers comprise a wide variety of differing protein structures Klug A, Rhodes D. Zinc fingers: a novel protein fold for nucleic acid recognition. Cold Spring Harb Symp Quant Biol 1987: 52:473-82. PMID: 3135979). The vast majority of zinc finger proteins bind DNA, RNA, proteins, or other molecules; their structural variations primarily alter their binding specificity. ZNFs are generated by fusing a zinc finger DNA-binding domain to a DNA-cleavage domain. This enables ZNFs to target unique genome loci and invoke endogenous DNA repair mechanisms. ZNFs can thus precisely alter the genomes of higher organisms (Jabalameli H R et al. Gene 2015; 558:1-5) for therapeutic purposes.

Another tool for gene therapy derives from a molecular system that defends prokaryotes against foreign genetic material: CRISPRs (clustered regularly interspaced short palindromic repeats) are DNA loci containing short repetitions of base sequences, with each repetition being followed by short segments of spacer DNA from previous viral exposure (Marraffini L A and Sontheimer E J. Nat Rev Genet 2010; 11:181-90). They are found in approximately 40% of sequenced bacteria genomes (CRISPR Data Base: http://crispr.u-psud.fr/crispr/CRISPRdatabase.php), are often associated with cas genes that encode CRISPR-related proteins and, as the CRISPR/Cas system, form a prokaryotic system for acquired immunity against foreign genetic elements such as plasmids and phages (Barrangou R et al. Science 2007; 315:1709-12; Mali P et al. Nature Methods 2013:10:957-63). CRISPR spacers recognize and cut such exogenous gene material in a manner similar to eukaryotic RNA interference (Marraffini L A and Sontheimer E J. Nat Rev Genet 2010; 11:181-90). The CRISPR/Cas system has been used for gene editing and gene regulation (Mali P et al. Nature Methods 2013:10:957-63). By cellular delivery of Cas9 and appropriate guide RNAs, the target organism's genome can be cut at any desired location (Esvelt K M et al. elife 2014:e03401). The CRISPR/Cas system divides into the three major types I, II, and III as well as twelve subtypes (Ain Q U, Chung J Y, Kim Y H. J Control Release 2015; 205:120-127).

Alternatively, transcription activator-like effector nucleases (TALENs) are artificially engineered restriction enzymes generated by fusing the DNA-binding domain of a transcription activator-like effector (TALE) to a DNA cleavage domain that can specifically bind to any desired DNA sequence for genome editing (Boch J. Nature Biotech 2011; 29:135-6) and, hence, genetic intervention (Ain Q U et al. Control Release 2015; 205:120-127). TALENs have been utilized experimentally to correct genetic errors underlying disease (Carlson D F et al. Mol Ther Nucleic Acids 2012; 1:e3).

Tools for Gene Silencing or Post-Transcriptional Regulation of Gene Expression

Gene silencing down-regulates the expression of a certain gene. According to the present invention, tools for transcriptional gene silencing or post-transcriptional regulation of gene expression include microRNAs (miRNAs), antisense oligonucleotides, small interfering RNAs (siRNAs), and messenger RNAs (mRNAs). For clearness, gene silencing is synonymous to gene knockdown (with a reduction in gene expression of 70%), while gene knockout—as by meganucleases—completely eliminates the respective gene from the given genome (with 100% reduction in gene expression) siRNA has a central role in RNA interference, i.e. in gene regulation via posttranscriptional gene silencing. To this end, siRNA forms, together with certain protein components, the RNA-induced silencing complex (RISC). If the siRNA lead strand is engaged by a complementary mRNA, the mRNA is either degraded or its translation into a protein is blocked (Siomi H and Siomi M C. Nature 2009; 457:396-404). This function can be employed for therapeutic down-regulation of the expression of a disease-associated gene.

miRNAs are evolutionarily conserved small non-coding RNAs that can regulate gene expression. Increasing evidence supports a role for miRNAs in many human diseases, including cancer and autoimmune disorders. The function of miRNAs can be efficiently and specifically inhibited by antisense oligonucleotides, supporting their potential as targets for the development of novel therapies. Therefore, miRNA is a tool for gene silencing that is increasingly used to produce therapeutics to combat cancer and diseases, such as infectious diseases and neurodegenerative disorders.

Antisense oligonucleotides are synthetic single strands of DNA or RNA that are complementary to a chosen gene or gene expression sequence in the sense direction. Antisense DNA binds to protein-encoding or non-coding complementary RNA; in case of binding, the DNA/RNA hybrid is degraded by RNase H. Antisense RNA prevents protein translation by binding to complementary messenger RNA (mRNA). Antisense oligonucleotides can be employed for antisense therapy of genetic disorders. In this case, the complementary antisense oligonucleotide binds to the mRNA produced by the respective gene thus posttranscriptionally turning the gene off before translation into its disease-associated protein. Alternatively, an antisense oligonucleotide may bind to a splicing site on the pre-mRNA. Antisense oligonucleotides have been investigated as potential drugs for diseases cancers (e.g., lung cancer, colorectal carcinoma, pancreatic carcinoma, malignant glioma, and malignant melanoma), diabetes, amyotrophic lateral sclerosis, Duchenne muscular dystrophy and diseases such as asthma, (Goodchild J. Chapter I. Therapeutic arthritis and pouchitis with an inflammatory component Oligonucleotides. In: Goodchild J. (ed.). Methods in Molecular Biology: Therapeutic Oligonucleotides. Methods and Protocols. Springer 2011: ISBN 978-1-61779-188-8. Pp. 1-15.). In 2014, the U.S. Food and Drug Administration (FDA) approved two antisense drugs, i.e. Fomivirsen (Vitravene®) for treating cytomegalovirus retinitis and Mipomersen (Kynamro®) against homozygous familial hypercholesterolemia. There is also interest in the use of antisense drugs to treat several neurodegenerative disorders Nevertheless, sense oligonucleotides have also been shown to exert therapeutic activity, such as against the human immunodeficiency virus (HIV) where viral propagation was inhibited by a sense 20-mer oligodeoxynucleotide directed against the 5'-tat splice acceptor site of the virus (Sullivan S M et al. Antisense Res Dev 1992; 2:187-97).

mRNA has a long-known function as the transcript of a given gene that is further translated into a peptide or protein product. If, in a hereditary disorder, a gene is either dysfunctional or missing completely, the introduction of the respective mRNA into an affected cell may compensate for this defect. Hence, delivery of such mRNA to the respective cell can be considered as posttranscriptional regulation of gene expression.

Targeted Delivery of Gene-Therapeutic Agents

Nanocarriers

As mentioned above, nucleic acids are not very efficient when administered in free form. Thus, their successful application for treating diseases requires to employ nanocarriers that allow the therapeutic nucleic acids to safely and efficiently reach their target. Thus, the inventors established another models of targeted drug delivery, i.e. by their encapsulation within nanocarriers addressed to the cell of interest. Such targeted nanocarriers for gene-therapeutic applications are specified in the present application.

In a preferred embodiment, the present invention relates to hepatocyte-specific nanocarriers encapsulating either mRNA or DNA for translation or expression in hepatocytes, respectively.

Non-viral nanoparticles—or nanomedicines—are subdivided into lipid-based/organic and non-lipid-based/inorganic nanocarriers. Surface modifications make them suitable for targeted delivery of drugs and their controlled release into cells or to tissues and organs. Lipid-based nanocarriers include, but are not limited to, liposomes, lipoplexes, and micelles. Non-lipid-based nanoparticles include, but are not limited to, synthetic polymeric nanoparticles [e.g., poly(D,L-lactic-co-glycolic acid) nanoparticles], dendrimers, carbon nanotubes, and colloidal gold nanoparticles (i.e., gold nanoshells and gold nanocages).

In a preferred embodiment of the present invention, the systemic properties of nanoparticular drug carriers can be altered by coating their surface with polyethylene glycol (PEG; MW<20,000 g/mol). PEG is an oligomer or polymer of ethylene oxide [H—(O—CH$_2$—CH$_2$)$_n$—OH]. Depending on its molecular weight, this polyether compound is also known as polyethylene oxide (PEO; MW>20,000 g/mol) or polyoxyethylene (POE; any molecular mass). Geometrically, PEGs are (i) branched PEGs (with 3-10 PEG chains emanating from a central core group), (ii) star PEGs (10-100 PEG chains emanating from a central core group), and (iii) comb PEGs (with multiple PEG chains linked to a polymer backbone). Most PEGs come as a mixture of molecular weights and thus are polydisperse. Their size distribution is characterized statistically by weight average molecular weight (Mw) and number average molecular weight (Mn) (both of which can be measured by mass spectrometry); their ratio is termed polydispersity index (Mw/Mn). The nonionic starch derivative hydroxyethyl starch (HES) is yet another type of molecule that, like PEG, can serve as a "shielding agent" for nanocarriers. It thus is not only has medical value as a volume expander, which is its most frequent use. Besides single molecules, nanocarriers can be PEGylated by covalent coupling, hence prolonging their circulation in the bloodstream and altering their pharmacokinetics and biodistribution as well as reducing their opsonization by blood-borne proteins leading to subsequent non-specific uptake by mononuclear phagocytes.

Targeting Moieties, Cellular Receptors, Target Cells, and Indications

According to the present invention, examples for targeting moieties linked to nanocarriers are peptides, carbohydrates or rather carbohydrate residues, antibodies and fragments thereof, other (glyco)proteins, and aptamers. More specifically, the carbohydrate residue is based on a monovalent or multivalent, linear or branched fucose or galactose or N-acetylgalactosamine (GalNAc), or on the natural polysaccharide chitosan. Even more specifically, targeting anchors may be structures embedded within or covalently linked to a nanocarrier in which the cell-specific targeting moiety is a carbohydrate, an antibody or an antibody fragment, a non-antibody protein derivative, an aptamer, a lipoprotein or a fragment thereof, a peptidoglycan, a lipopolysaccharide or a fragment thereof, or a CpG DNA (wherein the CpG sequence motive stands for 'cytosine-phosphate-guanine'). Among these, carbohydrate-based anchors can be monovalent or multivalent derivatives of fucose (i.e. of D,L-fucose, of D-fucose, or of L-fucose) or mannose (i.e. of D,L-mannose, of D-mannose, or of L-mannose). Such sugars are recognized by C-type lectin receptors (CLRs) and can thus be utilized to address myeloid antigen-presenting cells for therapeutically addressing viral, bacterial, fungal, and parasitic infections. or for many other therapeutic options that involve CLRs wherein these receptors allow for uptake of active agents, for vaccines, or for triggering distinct signaling pathways that induce the expression of specific cytokines which determine T cell polarization fates—and, hence, a broad array of antigen-specific immune responses. Other carbohydrates suitable as a targeting moiety installed on nanocarriers are hepatocyte-specific carbohydrates, such as galactose (i.e. of D,L-galactose, of D-galactose, or of L-galactose) or N-acetylgalactosamine (GalNAc), that allow to selectively address hepatocytes for various therapeutic applications. Next, aptamers can be used as targeting moieties. Aptamers are short (i) oligonucleotides (DNA or RNA or XNA) or (ii) peptides that bind to specific molecular targets. To date, aptamers have been particularly employed as active targeting moieties for targeted delivery of therapeutic anti-cancer agents. Moreover, according to the present invention certain bacterial products may qualify as targeting moieties due to their pathophysiological binding properties. Including lipoproteins (or fragments thereof), peptidoglycans, lipopolysaccharides (or fragments thereof), as well as CpG DNA, these bacterial products are recognized by certain cells via their Toll-like receptors (TLRs). As they are specifically recognized by TLR-1 (binding bacterial lipoproteins and peptidoglycans), TLR-2 (binding bacterial peptidoglycans), TLR-4 (binding bacterial lipopolysaccharides), TLR-6 (binding bacterial lipoproteins), and TLR-9 (recognizing CpG DNA) they can be utilized to target cells or families of cells expressing exactly these TLR variants.

Inevitably, examples for targeting moieties or rather targeting ligands must remain incomplete as virtually any type of molecule—whether a naturally occurring biomolecule, a modified biomolecule, or an artificial molecule—that is able to bind to a given surface structure of interest may serve as a targeting moiety or rather targeting ligand for a nanocarrier.

In a preferred embodiment of the present invention, hepatocyte-specific targeting ligands are used that allow to selectively address hepatocytes for various therapeutic applications. For example hepatocyte-specific carbohydrates, such as galactose (i.e. of D,L-galactose, of D-galactose, or of L-galactose) or N-acetylgalactosamine (GalNAc), that allow to selectively address hepatocytes are used as a targeting moiety installed on nanocarriers. Furthermore, according to the present invention, a hepatocyte-targeting glycolipid is used. The glycolipid is based on the overall molecular structure earlier described by Gieseler R K et al. Mar. 21, 2005. WO/2005/092288, for example, cholesten-5-yloxyl-N-(4-((1-imino-c-b-D-thio[CHO*]ethyl)amino) butyl)formamide (*wherein "CHO" stands for either of the afore-mentioned monosaccharides). However, the carbohydrates mentioned therein are replaced by D,L-galactose, D-galactose, L-galactose, or GalNAc, or by combinations or permutations thereof.

Targeting moieties may be linked covalently directly to the nanocarrier. Alternatively, the targeting moiety may be attached to the nanocarrier via a spacer and, particularly, a polyethylene glycol (PEG) spacer of suitable molecular size or hydroxylethyl starch (HES) so as to beneficially alter the properties of the targeted drug delivery system (see also above). Other types of linkers or spacers that may or may not be combined with PEG are 3,4,5-trihydroxy-6-(hydroxymethyl)tetrahydro-2H-pyran-2-yl)thioureido)butyl)carbamate, N-hydroxysuccinimide (NHS), 1,2-distearoyl-sn-glycero-3-phosphoethanolamin-N-[poly(ethylenglycol)-2000]-N-hydroxysuccinimid (DSPE-PEG-NHS), ε-aminocaproic acid (a.k.a. 6-aminocaproic acid), polyaldehydes, polyolefins, polyethylene oxide, poly-ω-alkenoic acid esters, or polyalkyl methacrylate.

Targeting moieties specifically bind to receptor molecules expressed on the surface of the respective target cells or cell species. These target cells or cell species comprise (i) stem cells, with pluripotent stem cells (including induced pluripotent stem cells), multipotent stem cells, cord-blood stem cells, hematopoietic stem cells, mesenchymal stem/stromal cells, neural stem cells, tumor stem cells, and rare stem cell populations in anatomical niche locations; (ii) immune cells, with myeloid antigen-presenting cells (monocytes, immature or mature dendritic cells, Langerhans cells, and macrophages), non-myeloid antigen-presenting cells (plasmacytoid dendritic cells), and antigen-presenting cells of unclarified ontogeny (follicular dendritic cells), T lymphocytes (thymocytes, T cells expressing αβ-T-cell receptors (TCRs) or γδ-TCRs, regulatory T (Treg) cells, T-helper cells, cytotoxic T cells, natural killer T (NKT) cells, and T-memory cells), B lymphocytes [progenitor (pre-pro) B cells, pro-B cells, pre-B cells, immature B cells, mature B cells, B plasma cells, and B-memory cells), and natural killer (NK) cells of the innate immune system; (iii) liver cells, with hepatocytes, such as primary hepatocytes, e.g. primary human hepatocytes; hepatic stellate cells (a.k.a. Ito cells), such as human LX-2 hepatic stellate cells; hepatoma cells, such as human HepG2 hepatoma cells; and hepatic sinusoidal endothelial cells; (iv) pneumocytes, with type I and type II pneumocytes; (v) myocytes; (vi) neurons and glial cell, with astrocytes, oligodendrocytes, and microglial cells; (vii)

keratinocytes; (viii) fibroblasts; (ix) chondrocytes; (x) exocrine glandular cells, with goblet cells, Paneth cells, Brunner cells, parathyroid Chief cells, pancreatic centroacinar cells, cuboidal mammary cells, and prostate glandular cells (xi) endocrine glandular cells, with thyroid epithelial cells, parafollicular cells, adrenal cortical cells, pancreatic α, β, γ and δ cells, ovarian endocrine cells, and testicular endocrine cells; (xii) endothelial cells, with variants of such cells that line the interior surface of regular blood vessels, of the brain capillary endothelium forming the blood-brain barrier, and of the interior surface of lymphatic vessels; and (xiii) epithelial cells with their squamous, columnar, cuboidal, and pseudostratified variants. Cellular receptors can either be regular markers on the surface of a healthy target cell. However, targeting moieties are of particular interest when they enable to address altered receptors on diseased cells resulting from the malign degeneration, infection or other pathological alteration of any of the healthy stem cells or somatic cells mentioned above in that they show significantly increased expression or are expressed de novo when compared to their healthy counterparts.

In a preferred embodiment of the present invention, liver cells, with hepatocytes, such as primary hepatocytes, e.g. primary human hepatocytes; hepatic stellate cells (a.k.a. Ito cells), such as human LX-2 hepatic stellate cells; hepatoma cells, such as human HepG2 hepatoma cells; and hepatic sinusoidal endothelial cells are used as target cells or cell species. More preferably, primary human hepatocytes are used as target cells or cell species.

Such a disease-related marker is expressed on the surface of the diseased cells in (i) malignant diseases—including, but not limited to, cancer of the lungs and bronchi, colon and rectum, urinary bladder, melanoma, non-Hodgkin lymphoma, kidney and renal pelvis, pancreas, liver (including hepatocellular carcinoma (HCC) or cholangiocarcinoma (CCC)), thyroid (including non-medullary and medullary thyroid carcinoma), breast, prostate and ovary; (ii) autoimmune diseases—including, but not limited to, Sjögren's syndrome, systemic lupus erythematosus, autoimmune thyroid disease (including Graves' disease together with Graves' orbitopathy and Hashimoto's thyroiditis), scleroderma, juvenile idiopathic arthritis, rheumatoid arthritis, multiple sclerosis, psoriasis, Wegener's granulomatosis, ankylosing spondylitis and autoimmune diseases that are related to the liver (including autoimmune hepatitis (AIH), primary sclerosing cholangitis (PSC) and primary biliary cirrhosis (PBC)); (iii) inherited disorders—including, but not limited to, Angelman syndrome, Canavan disease (a.k.a. Canavan-van Bogaert-Bertrand disease), a leukodystrophy), Charcot-Marie-Tooth disease, cystic fibrosis (a.k.a. mucoviscidosis), Duchenne muscular dystrophy, hemochromatosis, e.g. hemochromatosis type 1 (a.k.a. HFE-related hereditary hemochromatosis), hemophilia A, hemophilia B, neurofibromatosis, phenylketonuria, polycystic kidney disease, sickle-cell disease, and Tay-Sachs disease; (iv) metabolic disorders—including, but not limited to, type 2 diabetes mellitus (DM1), alcoholic fatty liver disease and non-alcoholic fatty liver disease (NAFLD), alcoholic steatohepatitis and non-alcoholic steatohepatitis (NASH), hepatitis A, B, C, D and E, type I glycogen storage disease (GSD I; a.k.a. von Gierke's disease), mucopolysaccharidoses, and lipid storage diseases (a.k.a. lipidoses); and (v) infectious diseases caused by a virus (e.g., HIV-1, HIV-2, HBV, HCV, HDV, HCMV, EBV, either of the influenza viruses, corona virus, Dengue virus, Ebola virus, and Marburg virus), an obligate or a facultative bacterium (*Mycobacterium tuberculosis, M. leprae, Legionella pneumophila, Francisella tularensis, Yersinia pestis, Coxiella burnetti, Rickettsia* spp., *Rickettsia rickettsia, Salmonella* spp., *Escherichia coli, Listeria monocytogenes, Neisseria* spp. *Brucella* spp., and *Shigella* spp.), a fungus (e.g., *Pneumocystis jirovecii* and *Histoplasma capsulatum*), or a protozoan (e.g. *Plasmodium* spp., *Toxoplasma gondii, Cryptosporidium parvum, Leishmania* spp., and *Trypanosoma cruzi*).

Novel nanomedicines have an immense potential for significantly improving cancer treatment. Nanoconstructs such as liposomes are widely used in clinics, while polymer micelles are in advanced phases of clinical trials in several countries. In the past years, receptor-mediated tumor targeting has received major attention as it improves the pharmacokinetics of various drugs and protects the patient from systemic toxicity and adverse effects that result from the non-selective nature of most current cancer therapeutic agents. Specific receptors allowing for uptake of a drug-loaded targeted nanocarrier include, but are not limited to tumor-associated antigens categorized as (i) hematopoietic differentiation antigens (CD20, CD30, CD33, and CD52); (ii) cell surface differentiation antigens (various glycoproteins and carbohydrates); (iii) growth factor receptors (CEA, EGFR/ErbB1, HER2/ErbB2, c-MET/HGFR, IGFR1, EphA3, TRAIL-R1, TRAIL-R2, RANKL; (iv) vascular targets (VEGFR, αVβ3, α5β1). Depending on safety considerations, some of these antibodies as well as some of the natural ligands of cancer-associated receptors may be of substantial additional benefit when being employed as the targeting moieties of nanomedicines.

There is a range of serious liver diseases with a high prevalence and an immense medical need for better treatment methods. Prominently, these diseases include non-alcoholic fatty liver disease (NAFLD), non-alcoholic steatohepatitis (NASH) and hepatocellular carcinoma (HCC). As to the present invention, all these disorders have a common denominator in that they offer various targets for gene-therapeutic intervention; they may thus be addressed therapeutically with hepatocyte-specific drug-delivery systems that carry genetic payloads. NAFLD has evolved as a serious public health problem in the Western and the westernized countries around the world. In fact, NASH—the most serious form of NAFLD—is predicted to become the leading cause of liver transplantation in the USA by the year 2020. The pathogenesis of NAFLD and NASH, in particular the mechanisms responsible for liver injury and fibrosis, is at the center of intense investigation. Likewise, HCC is a major health problem worldwide and the third most common cause of cancer-related death. Despite the fact that HCC treatment decisions are complex and dependent upon tumor staging, Bertino and colleagues elaborated that molecularly targeted inhibitors of tumor signaling pathways and immunotherapy-like vaccines against tumor-associated antigens may be essential components of the most effective therapeutic options in the future (Bertino G et al. Biomed Res Int 2015; 2015:731469). Both of which can be realized by targeted suitable nucleic acids that are preferentially delivered by the method of the present invention. For example, Rajeev et al. showed that siRNAs conjugated to triantennary N-acetylgalactosamine (GalNAc) as well as to monovalent GalNAc units—via uptake mediated by the asialoglycoprotein receptor (ASGPR)—induce robust RNAi-mediated gene silencing in the liver. (Rajeev K G et al. Chembiochem 2015; 16:903-8). This efficiency of the introduction of a gene-therapeutic agent may be significantly increased by the method of the present invention, i.e. by using nanocarriers featuring targeting moieties of multiantennary GalNAc.

Specifically for HCC, one of the most common cancers worldwide, instillation of the drug-loaded nanocarrier by hepatic artery infusion may at least in a certain percentage of patients be the route of choice.

Thus, since primary human hepatocytes are preferably used as target cells or cell species, the following diseased cells are preferable targeted according to the present invention, cells in (i) malignant diseases of the liver or rather cancers of the liver, such as hepatocellular carcinoma (HCC) and cholangiocarcinoma (CCC); in (ii) autoimmune diseases that are related to the liver, such as autoimmune hepatitis (AIH), primary sclerosing cholangitis (PSC) and primary biliary cirrhosis (PBC); in (iii) inherited disorders that are related to the liver, such as hemochromatosis, e.g. hemochromatosis type 1 (a.k.a. HFE-related hereditary hemochromatosis); and in (iv) metabolic disorders that are related to the liver, such as alcoholic and non-alcoholic fatty liver disease (NAFLD), alcoholic and non-alcoholic steatohepatitis (NASH), and hepatitis A, B, C, D, and E; more preferably cells in HCC, NAFLD and NASH.

In order to enable encapsulated actives to address cells in the central nervous system, the chosen targeted drug delivery system has efficiently to cross the blood-brain barrier (BBB). The BBB acts as a physical barrier that prevents free entry of blood-derived substances, including those intended for therapeutic applications. Non-invasive delivery of therapeutics into the brain may be realized by applying targeted drug delivery tools that enable to ferry active agents across the BBB via receptor-mediated transcytosis. In this process the nanocarrier-drug system is transported transcellularly across the brain endothelium, from the blood to the brain interface. In this regard, the inventors have shown in the present application that carriers furnished with C-type lectin-specific targeting receptors do as well cross the BBB to a certain extent. Another option is chitosan as a targeting molecule. This biocompatible natural linear polysaccharide composed of randomly distributed β-(1-4)-linked D-glucosamine and N-acetyl-D-glucosamine has been used in targeted drug delivery for treating neurodegenerative disorders. Chitosan and its biodegradable products are bioactive on nerve cells and the BBB, which is beneficial in treating Alzheimer's disease. In the form of nano-complexes, chitosan has been used for delivering anti-Alzheimer's drugs and siRNA to the brain (Sarvaiya J and Agrawal Y K. Int J Biol Macromol 2015; 72:454-65).

With respect to the present invention, the human disease entity is one that can be treated or may be cured by targeted genome editing, genome silencing or the post-transcriptional regulation of gene expression upon targeted delivery of the variant of nucleic acid to be chosen. Stem cells are a special case in that these cells are not diseased by themselves but may be harnessed for cell-based therapies in the context of regenerative or reparative medicine.

The mode of delivery of the nanocarrier-encapsulated or -associated active agent may be intravenous, subcutaneous, intradermal, intraperitoneal, parenteral, intrapulmonary (e.g., via an aerosol), by infusion via the hepatic artery, intrathyroidal, intranasal for pulmonary delivery, intranasal for nose-to-brain delivery, intrathecal, to the posterior eye segment, by intravitreal application, or in the case of stem cells by direct cellular ex-vivo treatment followed by re-inoculation of such treated autologous cells into a patient.

Finally, in order to achieve the best possible therapeutic result for a patient it may be beneficial either (i) to combine two or three nanocarriers with identical targeting moieties yet loaded with different gene-therapeutic tools, (ii) to combine two or three nanocarriers having different targeting moieties that are loaded with the same gene-therapeutic tool, or (iii) to combine two or three nanocarriers having different targeting moieties that are loaded with different gene-therapeutic tools. In the latter case, (i) either the same target cell is recognized by different cellular receptors via different targeting moieties, so that different gene-therapeutic tools are introduced into said cell for producing a complementary therapeutic response, or (ii) different target cells are recognized by distinctive different cellular receptors via different targeting moieties, so that different gene-therapeutic tools are introduced into different cells or cell differentiation stages (such as in the metastatic progression of a malignant disease) or into different cells that are affected by different stages of the same disease so as to produce an optimized therapeutic response.

The option of combining complementary permutations of targeting systems and active agents is a desideratum of (evidence-based) personalized medicine, wherein this approach may be guided by pharmacogenomics and/or chronopharmacological 15 considerations (Sharma S. Nanotheranostics in evidence based personalized medicine. Curr Drug Targets 2014; 15:915-30.).

The preparation of the nanocarriers is within the knowledge of the person skilled in the art. For example, nanocarriers are formulated according to a basic protocol published before (Gieseler R K et al. Mar. 21, 2005. WO/2005/092288; Gieseler R K et al. Scand J Immunol 2004; 59:415-24. PMID 15140050). However, protocols may be modified in that the densities of targeting anchors were employed in the range of 5% to 10% surface density of a fucose-derivatized anchor (for addressing cells via C-type lectin receptors expressed on their surface) or of 5-10% of a galactose-derivatized anchor (for addressing cells via asialoglycoprotein receptor expressed on their surface). In addition, the liposomal composition may be modified using phosphatidyl choline (PC), 1,2-dioleoyl-sn-glycero-3-phosphocholine (DOPC), 1,2-dioleoyl-sn-glycero-3-phosphoethanolamine (DOPE), 1,2-dioleoyl-3-trimethylammonium-propane (DOTAP), cholesteryl hemisuccinate (CHEMS), soy phosphatidylcholine (SPC-3), and cholesterol—each at a purity of >99% —at different molar ratios so as to arrive at a protocol that generates nanocarriers allowing for endosomal release of an encapsulated gene-therapeutic payload within the targeted cells.

EXAMPLES

On the example of HIV-1, the gene-therapeutic approaches described herein were to inhibit viral propagation (i) through genome editing via plasmid-encoded TALEN activity or (ii) via blockade of a selected viral gene by sense or antisense oligonucleotides. Infection with HIV-1 can be used as an example as the viral genome is integrated into the host genome as a so-called HIV-1 provirus. The same methods, or variants thereof, can be transferred to or adapted to other indications.

A. Studies Employing Plasmid DNA

Example 1: Targeted Lipid-Based Nanocarriers

Nanocarriers were formulated according to a basic protocol published before (Gieseler R K et al. Mar. 21, 2005. WO/2005/092288; Gieseler R K et al. Scand J Immunol 2004; 59:415-24. PMID 15140050). However, protocols were modified in that the densities of targeting anchors were increased to 8% surface density of a fucose-derivatized anchor (for addressing cells via C-type lectin receptors expressed on their surface) or 8% of a galactose-derivatized anchor (for addressing cells via asialoglycoprotein receptor expressed on their surface). In addition, the liposomal composition was modified using phosphatidyl choline (PC), 1,2-dioleoyl-sn-glycero-3-phosphocholine (DOPC), 1,2-dioleoyl-sn-glycero-3-phosphoethanolamine (DOPE), 1,2-dioleoyl-3-trimethylammonium-propane (DOTAP), cholesteryl hemisuccinate (CHEMS), soy phosphatidylcholine (SPC-3), and cholesterol—each at a purity of >99% —at different molar ratios so as to arrive at a protocol that generates nanocarriers allowing for endosomal release of an encapsulated gene-therapeutic payload within the targeted cells.

Example 2: Encapsulation of Plasmid DNA into Nanocarriers

DNA in the form of plasmids (p-DNA) either encapsulated the gene encoding for green fluorescent protein (GFP) as a reporter gene or the sequence encoding for TALEN. Encapsulation of DNA was initially performed as based on earlier protocols (Pupo E et al. J Contr Release 2005; 104:379-96; Bailey A L and Sullivan S M. Biochim Biophys Acta 2000; 1468:239-52). However, protocols were modified in that the parameters for the formulation of multilamellar vesicles (MLVs) from which small unilamellar vesicles (SUVs) were generated, and high-pressure homogenization (extrusion: 50 nm or 100 nm) were modified. In addition, speed-mixing was introduced as a method for increasing the encapsulation rate so as to eventually allow for acceptable payload encapsulation rates. Non-encapsulated DNA payload was removed by dialysis from the phosphate buffer in which the nanocarriers were dissolved. However, it may be a future option to omit the dialysis step as freely soluble nucleic acids are usually degraded quickly in the circulation and thus are not expected to cause any adverse effects. Omission of dialysis would reduce time and cost requirements.

Example 3: Analytics

The inventors determined the size (mean and distribution) by photon correlation spectroscopy (PCS), the total lipid content by high-performance thin layer chromatography (HPTLC), and payload encapsulation efficiency by quantitative polymerase chain reaction (q-PCR).

Example 4: Characteristics of DNA-Loaded Nanocarriers

A total of 65 nanocarrier variants featuring fucosylated targeting anchors and different membrane compositions were formulated. With these batches, we evaluated a great number of variations in the general production process, in the liposomal components and in the establishment of a functional methodological approach for determining the encapsulation efficiency of nucleic acid. The initial batches were produced specifically for the optimization of different process-related steps. Of the different membrane compositions tested, the final protocol employed variants of molar ratios including, with one variant specified as 45.95% DOPC, 45.95% DOPE, and 8% fucosylated anchor material, loaded with 26 µg pEGFP mRNA or either 50 µg or 100 µg TALEN-encoding p-DNA. By quantitative polymerase chain reaction (q-PCR), we received a DNA encapsulation efficiency (i.e., DNA encapsulated into nanocarriers of the initially employed DNA amount) of 20-43% with a DNA loading capacity (i.e., mass of DNA per mass of lipid) of 0.00117-0.00214. Table 1 shows select representative specifications, including their mean sizes in nanometers, for nanocarriers formulated. FIG. 1 shows the DNA encapsulation rates.

TABLE 1

Specifications for nanocarriers encapsulating DNA. Inhibition of HIV-1 p24 production.

| Property | method | target value | result | remark |
| --- | --- | --- | --- | --- |
| Z-Average | PCS | <200 nm | 170.6 nm | conforms |
| d (main component) | PCS | <200 nm | 188.8 nm | conforms |
| Polydispersity | PCS | <0.3 | 0.218 | conforms |
| ζ/mV | PCS | 0 mV | −18.2 | expected value for lipid composition |
| X(lipid component A) | HPTLC | 35.0% | | not determined |
| X(lipid component B) | HPTLC | 35.0% | | not determined |
| X(lipid component C) | HPTLC | 22.0% | | not determined |
| X(targeting ligand) | HPTLC | 8.0% | | not determined |
| c (lipids) | estimation | 11.00 mM | | |
| y (lipids) | estimation | 7.50 g/L | | |
| y (DNA) | estimation | 55 mg/L | | 50 µg in about 900 µL |

Cell supernatants (n = 3 for each condition) were measured for HIV-1 p24. Shown are the values measured on day 5 after treatment. On days 1 and 3, conditions showed only marginal differences, if any, with 6 ng/mL or 20 mg/mL, respectively. The sense condition led to inhibition of HIV-1 propagation, while the antisense condition did not.
SD: Standard deviation.
Concentrations in the cell culture conditions: Nanocarrier lipid: 100 µM; encapsulated DNA: 140 nM.

Concluding Remark on Genome Editing: Excision of HIV-1 provirus from the genome of a host cell enabled by a cell-targeted gene-therapeutic onset such as the one tested here may offer a significant step towards achieving a cure of HIV disease. The same applies to similar applications for other indications in which a genome-editing enzyme can be introduced.

B. Studies Employing Sense and Antisense Oligonucleotides

Example 5: Materials

Reagents and producers/vendors were (i) phospholipids (Avanti Polar Lipids, Birmingham, AL, USA); (ii) cholesterol and N-succinimidyl-S-acetylthioacetate (SATA) (Calbiochem, San Diego, CA, USA); (iii) phytohaemagglutinin (PHA) (PHA-P, Difco Laboratories, Detroit, MI, USA); (iv) mouse-anti-HIV-1 p17, mouse-anti-HIV-1 gp-p41, and rabbit-anti-mouse IgG (DuPont/New England Nuclear, Wilmington, DE, USA); alkaline phosphatase/anti-alkaline phosphatase (Dako, Carpinteria, CA, USA); calcein (Sigma Aldrich, St. Louis, MO, USA); (v) deacetylated 6-carboxyfluorescein (Molecular Probes, Eugene, OR, USA); p24 antigen capture ELISA (Abbott Laboratories, Abbott Park, IL, USA); the immunocytochemistry stain Vector red (Vector Laboratories, Burlingame, CA, USA); and the mounting medium Crystal Mount (Biomedia, Foster City, CA, USA). The synthetic oligonucleotides, i.e. the sense sequence (5'-ATTTTCAGAATTGGGTGTCG-3') and the complementary antisense sequence, were obtained from Epoch Pharmaceuticals (Redmont, WA, USA). Analysis by 20% polyacrylamide gel electrophoresis (PAGE) at 7 M urea yielded single bands indicative of >95% purity. Sense and antisense stocks and batches were subsequently sequenced in coded form by the supplier and were thus verified to represent the correct sense and antisense sequences for the HIV-1 5' tat splice acceptor site.

Example 6: Generation of Cytokine-Enriched Supernatants

Buffy coats were prepared from whole blood of healthy donors and purchased from the American Red Cross (Los Angeles, CA, USA). Peripheral blood leukocytes (PBLs) were isolated from HIV-1-negative blood donors by density gradient centrifugation over Lymphoprep (1.077 g/mL). T cells were isolated, irradiated (2,000 rad) and suspended in 80% RPMI 1610/20% Earle's salts, plus 10% fetal calf serum (medium 80/20/FCS) and seeded at $2\times10^6$/mL in Petri dishes. The cells were stimulated with phytohaemagglutinin (PHA). After 48 h, T cells were pelleted and the supernatant (T-SUP) was collected and frozen as aliquots at −20° C. until use. T-SUP was added to the culture medium (see below) at 25% (vol/vol).

Example 7: Uninfected PBL Pools

As described above, PBLs were isolated buffy coats from HIV-1-negative blood donors. Pooled PBLs from for donors, each, were frozen in liquid nitrogen in medium 80/20/FCS plus 10% dimethyl sulfoxide (DMSO) as HIV-1 propagation peaks at an earlier point in time when PBLs from frozen stocks are used rather than freshly isolated PBLs (Ulrich P P, Busch M P, el-Beik T Shiota J, Vennari J, Shriver K, Vyas GN. Assessment of human immunodeficiency virus expression in cocultures of peripheral blood mononuclear cells from healthy seropositive subjects. J Med Virol 1988; 25:1-10). Cells from these pools were used for up to four weeks.

Example 8: Propagation of HIV-1 (In-Vitro)

PBLs were isolated from EDAT-treated blood samples of eight HIV-1-positive patients as verified by HIV-1 p24 and PCR for HIV-1 gag. Samples were either processed within 60 min after venipuncture or stored for up to 3 h at 4° C. before processing. The cells were obtained by density gradient centrifugation (see above). Using 25 cm² tissue culture flasks, PBLs from HIV-positive patients were cultured at $2\times10^7$ with $2\times10^7$ viable PBLs from the frozen pool (see above) in 80/20/FCS plus 25% T-SUP at 5 mL per flask. Every 5 days, 1 mL of culture medium was replaced and added $5\times10^6$ uninfected pooled donor PBLs to increase viral propagation. Likewise every 5 days, the supernatants were monitored for HIV-1 p24 core antigen for a total period of 30 days.

Example 9: HIV-1 Inhibition by Oligonucleotide-Loaded Nanocarriers

Figure 2:
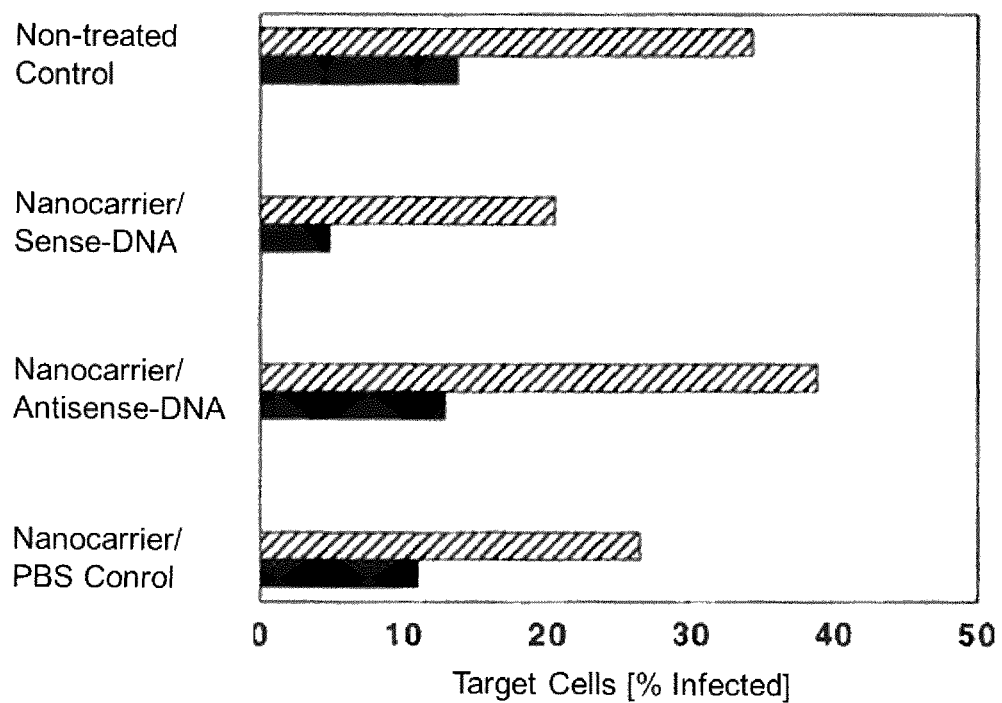
FIG. 2: Reduction in HIV-1-infected cells by sense oligonucleotides directed against the HIV-1 5' tat splice acceptor site. Cells expressing both HIV-1 core antigen p17 and envelope antigen gp41/gp160 were identified by immunocytochemistry, with 500 cells evaluated for each condition. Highly infected cells (black bars) were stained both in cytosol and cell membrane, while weakly stained cells were usually antigen-positive in the membrane only, and in some cases faintly in the cytosol. Percentages of total cells infected are shown as hatched bars. The reduction in the number of highly infected cells correlated strongly with the reduction in p24 levels in the supernatant. Nanocarriers loaded with the sense condition reduced the proportion of cells actively expressing HIV-1 by 71%. In contrast, the antisense condition yielded a 6% reduction, thus even lower than the control condition where nanocarriers were filled with PBS only with 18% reduction. Large cell aggregates—as typical of HIV-1-induced cell fusion—were observed under all conditions except for the sense condition. Thus, nanocarriers encapsulating sense oligonucleotides directed against the 5' tat splice acceptor site inhibited viral protein production by 84% and reduced the proportion of cells actively expressing virus by 71%. Therefore, the sense condition again led to inhibition of HIV-1 propagation, while the antisense condition did not.

Using 24-well tissue culture wells, each well received $2\times10^6$ uninfected door PBLs plus $2\times10^5$ patients' cells in of 80/20/FCS plus 25% T-SUP at 1 mL per well, further adding 1% albumin, 100 IU/mL of penicillin, 100 µg/mL of streptomycin, and 0.05 mg/mL of gentamicin. Cells were incubated for 3 h at 37° C., followed by addition of nanocarriers loaded with 5' tat sense, 5' tat antisense, or PBS only. During the subsequent 5-day incubation period, no medium was replaced and no further donor cells were added. On day 0 as well as days 1, 3, and 5 after onset, triplicate cultures were assayed for HIV-1 p24 (supernatant; by enzyme-linked immunosorbent assay [ELISA]), intracellular HIV-1 p17 and gp41 (see below for immunocytochemistry), and viability by trypan blue exclusion. Maximal saturating uptake by target cells of each of the three variants of nanocarriers, loaded with sense or antisense oligonucleotides or without payload, was found after 1 h (not shown). Oligonucleotide-loaded or non-loaded nanocarriers were added to cultures 1 h after viral inoculation addition. Results are shown in Table 2 and FIG. 2.

TABLE 2

Inhibition of HIV-1 p24 production

|  | HIV-1 p24 Production [ng/mL ± SD] (n = 3, each) | Inhibition of HIV-1 p24 Production [%] |
| --- | --- | --- |
| Untreated Control | 239 ± 25 | 0 (reference value) |
| Nanocarrier + Sense DNA | 39 ± 4 | −83.68 (mean) |
| Nanocarrier + Antisense DNA | 254 ± 16 | +6.28 (mean) |
| Nanocarrier: PBS Control | 232 ± 23 | −2.93 (mean) |

Cell supernatants (n = 3 for each condition) were measured for HIV-1 p24. Shown are the values measured on day 5 after treatment. On days 1 and 3, conditions showed only marginal differences, if any, with 6 ng/mL or 20 mg/mL, respectively. The sense condition led to inhibition of HIV-1 propagation, while the antisense condition did not.
SD: Standard deviation.
Concentrations in the cell culture conditions: Nanocarrier lipid: 100 µM; encapsulated DNA: 140 nM.

Example 10: Immunocytochemistry for HIV-1 p17 and Gp41

Cell specimens were transferred to slides, air-dried, fixed in acetone (5 min, 4° C.), and stored at −70° C. until evaluation. Slides were then brought to room temperature (RT), and the cells were re-hydrated in Tris-buffered saline (TBS) for 5 min and incubated with normal rabbit serum in TBS (NRS/TBS) for 30 min to reduce nonspecific binding. Mouse monoclonal antibodies against HIV-1 core antigen p17 and envelope antigen gp41 (cross-reacts with gp160) were added at a 1:1 ratio and incubated for 30 min at RT. Slides were washed ×3 with TBS and were then incubated with rabbit-anti-mouse IgG for 30 min at RT, and were then washed ×3 with TBS and processed through three cycles of alkaline phosphatase/anti-alkaline phosphatase (APAAP) (1:60 in NRS/TBS). Thereafter, cell preparations were immersed in Vector red for 20 min, rinsed with tap water, counterstained with hematoxylin, and mounted with Crystal Mount.

Concluding remark on Post-transcriptional Regulation of Gene Expression: The HIV-1 5' tat acceptor site was chosen because early on in HIV-1 research, the viral trans-activator protein expressed from this site had been shown to stimulate massive propagation of HIV-1 by action upon the viral long terminal repeat (Arya S K et al. Science 1985; 229:69-73; Green M and Loewenstein P M. Cell 1988; 55:1179-88; Frankel A D and Pabo C O. Cell 1988; 55:1189-93). It has since then become clear that replication-competent latent HIV-1 proviruses that persist in the genomes of memory T cells in infected individuals under life-long antiretroviral therapy are a major barrier towards viral eradication. Multiple molecular mechanisms are required to repress the viral trans-activating factor Tat and disrupt the regulatory Tat feedback circuit leading to the establishment of the latent viral reservoir (Mbonye U and Karn J. Virology 2014; 454-455:328-39). Hence, inactivation of the HIV-1 5' tat acceptor site by a cell-targeted gene-therapeutic onset such as the one tested here may offer a significant step towards achieving a cure of HIV disease. The same applies to similar applications for other indications in which a sense- or antisense-oligonucleotide approach applies and appears feasible.

Example 11: Development of a Hepatocyte-Targeted mRNA Formulation for Translation in Hepatocytes 1. Formulation Development Hepatotropic Targeting Ligand and Hepatocyte-Specific Nanocarriers A novel, human hepatocyte-specific targeting ligand (TL)—a hepatocyte-targeting glycolipid—was synthesized. In order to verify that TL could be integrated into our targeted liposomal platform (Gieseler R K et al. Mar. 21, 2005. WO/2005/092288; Gieseler R K et al. Scand J Immunol 2004; 59:415-24. PMID 15140050), four nanocarrier batches with varying molar fractions of TL (0%, 4%, 8%, or 12%, respectively) were formulated according to standard protocol (see previous citations). For reasons of comparability, conventional lipid compositions, DOTAP and cholesterol were employed. For tracing of uptake by target hepatocytes, nanocarriers contained 0.1% of the fluorescent dye, Texas Red 1,2-dihexadecanoyl-sn-glycero-3-phosphoethanolamine, triethylammonium salt (Texas Red-DHPE), in their bilayer. Nanocarrier batches were analyzed for mean particle size, particle size distribution, lipid content/composition, presence or absence of TL, and visual appearance (using PCS, evaluated by Malvern Zetasizer v7.11 software; and using HPTLC for determining nanocarrier components, evaluated by CAMAG Wincats 4 software). As the incorporation of TL did not significantly alter the nanocarriers' physical properties in comparison to hitherto produced nanocarriers, no changes in the established production and analytical processes were required. Batches were tested in-vitro for their cellular binding efficacy and efficiency (see below). Hepatocyte-specific nanocarriers are furthermore referred to as HEP-nanocarriers.

mRNA-Formulation: General Preparations

In order to prevent contamination with RNases, the study relied on semi-dedicated or dedicated material (Tab. 3), and on proper procedures for preventing contamination or decontamination procedures, respectively. Chemicals specifically reserved for formulating mRNA-encapsulating nanocarriers were fully dedicated. Labware was only used as semi-dedicated equipment if it can reliably be decontaminated. Decontamination included treatment with RNase AWAY solution, autoclaving with diethylpyrocarbonate (DEPC) water, or heat sterilization for at least 4 h at approximately 180° C.

TABLE 3

Materials for RNase Control.

| Item | Dedication Level |
|---|---|
| Lipid components | semi |
| Miniature extruder and extrusion membranes | full |
| Various glassware | semi |
| Various dialysis equipment/membranes | full |
| Organic solvents | semi |
| Pre-made buffer solution | full |
| DEPC | full |
| RNase AWAY ®, ready-to-use solution | full |
| Various labware | full/semi |
| Tips for direct displacement pipettes | full |

Semi-dedicated materials include chemicals that can be used or aliquoted without risk of contamination and can also be used for purposes unrelated to formulating mRNA-encapsulating nanocarriers.

2. In-Vitro Efficacy

The in-vitro targeting efficacy of HEP-nanocarriers (non-loaded) was tested in different types of hepatic cells as shown in Table 4. Primary hepatocytes were enriched from explanted human liver tissue kindly provided by the Department of General, Visceral, and Transplantation Surgery at the University Hospital Essen in Essen, Germany, and then cultured as detailed below. Liver cell lines were cultured according to protocols specified below. Cells were then targeted with HEP-nanocarriers or control batches and evaluated by immunocytochemistry.

TABLE 4

Test systems for in-vitro analyses of HEP-nanocarriers.

| Test System | Comment |
|---|---|
| 1. Primary Cells | |
| Primary hepatocytes | Isolated from healthy human liver |
| 2. Cell Lines | |
| HepG2 cells | Hepatoma cell line |
| LX-2 cells | Hepatic stellate cell line |

Primary Human Hepatocytes

Human liver tissue segments obtained intraoperatively were processed through several washes (Dulbecco's Phosphate Buffered Saline, DPBS; Hank's Buffered Salt Solution, HBSS) and perfused. Any tissue openings were sealed with Histoacryl so as to prevent any leakage of buffer or medium. Residual blood was flushed out with HBSS. Thereafter, a series of perfusions with (1) HBSS+ethylene glycol tetraacetic acid (EGTA) and (2) HBSS+$CaCl_2$ with collagenase were performed until the solid tissue completely turned into a cell dispersion. Cell solutions were passed through a sieve using 300-400 mL of HBSS. Cells were then distributed to various 50 mL Falcon tubes and spun at 300 rpm (18 g) for 10 min at RT. Resuspended pellets were merged in two 50 mL tubes and replenished to 50 mL with HBSS, and centrifuged (400 rpm; 10 min; room temperature, RT). Pellets were merged, refilled with HBSS, and spun once more (500 rpm, 10 min, RT). The pellet resulting from this final wash was dissolved in 30 mL Dulbecco's Modified Eagle's Medium (DMEM)/Ham's F12 medium+penicillin/streptomycin/gentamicin+10% fetal calf serum (FCS). Cells were set at 1×10⁶/mL. Alternatively, cells could be cultured in 6-well plates or 24-well plates. Plated cells were placed into an incubator for 1 h and were gently agitated every 10 min until complete sedimentation. The medium was then removed and replaced with fresh medium.

HepG2 Cells

Human HepG2 hepatoma cells (HepG2 cells) were cultured according to a protocol published in: Gieseler R K et al. J Viral Hepat 2011; 18:760-7. The cell line was initially reconstituted from frozen stock (−196° C.) and propagated to confluence in DMEM plus 10% FCS plus penicillin/streptomycin plus glutamine (HepG2 medium) in a 72 cm² flasks for seven days at 37° C., 95% relative humidity (RH). Cells were then detached (EDTA, 4° C.), washed twice with phosphate-buffered saline without $Mg^{2+}/Ca^{2+}$ (PBS), passaged once and propagated to confluence again in three 72 cm² flasks for five days in HepG2 medium. Thereafter, the cells were detached (EDTA, 4° C.) and washed again, counted in a Neubauer chamber, and seeded into two 96-well microtiter plates (MTPs) at $2×10^5$ cells/well at 200 µL HepG2 medium, each. For reconstitution of the surface receptor to be targeted, cells were incubated for 21 h to 22 h prior to treatment at 37° C. and 95% RH.

LX-2 Cells

Human LX-2 hepatic stellate cells (LX-2 cells) were cultured according to a protocol published in: Bechmann L P et al. Hepatol Res 2009; 39:601-8.

Hepatocyte Targeting

Cultured cells were targeted at between five and seven days of culture, depending on the status of the respective cell populations as assessed by light microscopy and trypan blue staining. Cells were incubated for 1 h at 37° C. and 95% RH under continuous gentle agitation at 1:10, 1:20 or 1:50 dilutions with the HEP-TargoSphere® batches or control nanocarriers indicated above and also specified in FIG. 2-1 NC, TS-1, TS-2 or TS-3. As mentioned above, all nanocarrier batches were labeled with Texas Red-DHPE. Triplicates were employed for each condition and immunocytochemical results (see next section) are given as arithmetic means of these triplicates.

Immunocytochemistry

Subsequent to incubation with HEP-nanocarriers or controls, immunocytochemistry was performed for the targeted endocytically active hepatocyte receptor (HepR) by direct immunocytochemistry (ICC) with a FITC-labeled monoclonal antibody labeled with fluorescein-5-isothiocyanate (FITC). Cells were counterstained with the nuclear dye 4′,6-diamidino-2-phenylindole (DAPI). Cells were then viewed and photographed via a Zeiss LSM510 META Confocal Imaging System and differentially evaluated for DAPI-positive cells, FITC-positive cells (hepatocytes), and cells positive for Texas Red-DHPE (hepatocytes successfully targeted). Cells were counted, with 100-200 cells per test condition or reading point, respectively.

Results

Primary Human Hepatocytes, HepG2 Cells, and LX-2 Cells without Payload

Primary hepatocytes were incubated with HEP-nanocarriers HEP-TargoSpheres for 1 h. Cells were then processed for immunocytochemistry and visualized under a Laser scanning microscope. Nuclear DAPI staining revealed all cells. Among these, maximum targeting of approximately 80.0% of hepatocytes (identified by Texas Red-DHPE) of cells expressing HepR (identified by FITC) was achieved when applying a 1:10 dilution (i.e. 5.7 mM) of the original dispersion of HEP-nanocarriers with 12% TL. Lower membrane densities of 4% or 8% of TL achieved targeting efficiencies of around 70% of the hepatocytes and may be sufficient for achieving a satisfactory transduction rate when delivering a mRNA. In contrast to cells incubated with TL-furnished HEP-nanocarriers, non-specific uptake of "naked" nanocarriers was around 7% after subtracting the autofluorescence. Differing from specifically targeted cells, these stains were weak only. Studies employing HepG2 hepatoma cells produced very similar results. As primary human hepatocytes are the benchmark for addressing such cells in-vivo and since the targeting of primary hepatocytes was carried out successfully, HepG2 cells served for control purposes only. The LX-2 hepatic stellate cell line used as a negative control was not addressed at all by the HEP-nanocarriers or any of the control conditions. In summary, the developed HEP-nanocarrier system may be employed for addressing the majority of healthy parenchymal liver cells.

HepG2 Cells Targeted with Cationic HEP-Nanocarriers Loaded with a Reporter mRNA

Before moving to the in-vivo level, HEP-nanocarriers were further optimized as to their strong vs. weak cationic charge. Protein expression from the reporter mRNA was quantified 24 h after incubation. At or above a dose of 1000 ng reporter mRNA, protein expression decreased due to cytotoxicity. At or below 100 ng reporter mRNA, a slightly higher expression of reporter protein was found for the more strongly cationic HEP-nanocarriers. The use of TL-furnished HEP-nanocarriers increased protein expression by approximately 2-fold when compared to non-targeted ("naked") nanocarriers.

Example 12. Development of a HEP-Nanocarriers Encapsulating DNA for Hepatocellular Expression The following experiments set out to determine whether delivering a plasmid DNA-encoded reporter gene (pRG) via HEP-nanocarriers to human hepatocytes would enable expression of reporter protein (RP) in-vitro, hence paving the path towards subsequent studies in animals treated with HEP-TargoSphere®-encapsulated pRG. The ultimate goal is to enable treatments for patients with either complete gene deficiencies or with genetic mutations leading to the absence of, or the production of defective or ineffective proteins, respectively.

HEP-Nanocarriers and Control Batches

Batches were formulated according to Rodos Biotarget's established formulation processes (see also above). The hepatocyte-specific targeting ligand (TL) was incorporated into HEP-nanocarriers at 8 mol %. All quality control measurements were in the acceptable tolerance ranges as determined by mean particle size, particle size distribution, lipid content and composition, presence or absence of TL, and visual appearance (see also above for greater detail).

HepG2 Cells and Nanocarrier Incubation

For reconstitution and culture of HepG2 cells, see above.

HepG2 cells were incubated for 2 h with appropriate dilutions of four batches to be compared, i.e. strongly or less strongly cationic HEP-TS or non-targeted nanocarriers, respectively, each loaded with pRG (see Tab. 5, below). HepG2 cells were then spun down using a plate rotor (260 g, 4° C.), nanocarrier-containing medium was removed, wells were washed with PBS, cells were spun down again, and wells were eventually replenished with 200 µL, each, of the HepG2 medium. Cells were kept for either 15 h or 22 h, respectively, before supernatants were harvested for determining the presence and activity of transcribed RP.

Importantly, free DNA as a control was not required. It has been demonstrated that, in contrast to nanocarrier-encapsulated DNA, 'naked DNA' leads to either no or only very low transfection and, if at all, shows the same protein expression as untreated controls (e.g., Birchall J C et al. Int J Pharm 1999; 183:195-207; Perrie Y et al. Vaccine 2001; 19:3301-10 and Balbino T A et al. Langmuir 2012; 28:11535-45. The only exception is seen upon intramuscular injection (e.g., Cohen H et al. Gene Ther 2000; 7:1896-905). As these findings were repeatedly confirmed in different systems, it is thus state of the art to omit a 'naked DNA' control.

Reference Protein Expression

The activity of RP was determined by a chromogenic assay. Briefly, in the presence of RP a chromogenic substrate is hydrolyzed to liberate a chromophore whose color is read photometrically at 405 nm. The color intensity is proportional to the RP activity. Using the FLUOstar Omega microplate reader (BMG LABTECH, Ortenberg, Germany), the absorbance of the material of the plates used (Cellstar, Cat. No. 655 180; Greiner Bio-One, Solingen, Germany) is compensated by the reader's software. A reference standard for RP was run in parallel to measuring the test samples. The reference standard was stored at −80° C. until usage and was reconstituted immediately before performing dilutions.

Treatment Conditions

HEP-nanocarriers and control carriers loaded with pRG are listed in Table 5.

TABLE 5

Treatment conditions.

| Formulation | Hepatocyte Targeting Ligand at 8 mol % | Amounts of pRG | Corresponding Nanocarrier Dilutions |
| --- | --- | --- | --- |
| HEP-nanocarrier #1: Strongly cationic | + | 0.5/1.0/2.5 µg | 1:50/1:25/1:10 |
| Control carrier #1: Strongly cationic | − | 0.5/1.0/2.5 µg | 1:50/1:25/1:10 |
| HEP-nanocarrier #2: Weakly cationic | + | 0.3/0.75/2.0 µg | 1:50/1:20/1:7.5 |
| Control carrier #2: Weakly cationic | − | 0.3/0.75/2.0 µg | 1:50/1:20/1:7.5 |

Results

Effect of Nanocarriers on HepG2 Cells

The cell line remained unimpaired at all times visualized under a microscope, i.e. after initial reconstitution, on day 7 of primary confluence, on day 5 of secondary confluence, after 21 h to 22 h incubation in microtiter plates, and after treatment with HEP-nanocarriers or non-targeted control batch. Hence, there was no indication of a toxic effect of the cationic nanocarriers within the observation period.

Strongly Cationic Nanocarriers

Strongly cationic nanocarriers led to both time- and concentration-dependent increase in RP expression and activity above untreated background values. There was almost no difference between hepatocyte-targeted and non-targeted pRG at 15 h post treatment, but clearly pronounced RP activities in HEP-TargoSphere®:pRG-treated HepG2 cells became apparent at 22 h after treatment.

The HEP-TargoSphere®: pRG condition was evidently superior to the non-targeted condition. Moreover, the targeted preparation showed a stronger increase in RP expression over time than the non-targeted control. Interestingly, this slope was most pronounced at the lowest dilution. The HEP-nanocarrier-dependent formulation was identified as the best condition.

Weakly Cationic Nanocarriers

Similar to the strongly cationic formulations, weakly cationic nanocarriers led to a time-dependent increase in RP expression and activity above untreated background values.

However, different from the strongly cationic nanocarriers, the concentration dependency reached saturation.

The difference between hepatocyte-targeted and non-targeted pRG at 15 h post treatment was more pronounced in favor of the targeted treatment than with the strongly cationic formulations. At 22 h after treatment, a clearly increased RP expression in HEP-TargoSphere®:pFVIII-treated HepG2 cells compared to the non-targeted condition was measured.

For the less cationic formations, calculated actual RP activities showed the same trends than with the strongly cationic conditions. However, activities were definitely lower. This might be explained by the saturation kinetics. Again, the hepatocyte-targeted formulation was identified as the best condition.

REFERENCE LIST

Patent References

Gieseler R K, Marquitan G, Scolaro M J, and Schwarz A. Carbohydrate-Derivatized Liposomes for Targeting Cellular Carbohydrate Recognition Domains of CTL/CTLD Lectins, and Intracellular Delivery of Therapeutically Active Compounds. Pub. No.: WO/2005/092288; International Application No.: PCT/US2005/009228. Publication Date: 6 Oct. 2005; International Filing Date: 21 Mar. 2005. IPC: A61K 38/16 (2006.01), A61K 47/48 (2006.01), A61K 9/127 (2006.01).

Non-Patent References

Aaldering L J, Tayeb H, Krishnan S, Fletcher S, Wilton S D, Veedu R N. Smart functional nucleic acid chimeras: Enabling tissue specific RNA targeting therapy. RNA Biol 2015; 12:412-25. doi: 10.1080/15476286.2015.1017234.

Allen T M. Liposomal drug formulations, Rationale for development and what we can expect for the future. Drugs 1998; 56; 747-56.

Arya S K, Guo C, Josephs S F, Wong-Staal F. Transactivator gene of human T-lymphotrophic virus type III (HTLV-III). Science 1985; 229:69-73. PMID 2990040.

Asprer J S, Lakshmipathy U. Current methods and challenges in the comprehensive characterization of human pluripotent stem cells. Stem Cell Rev 2015; 11:357-72. PMID 25504379. doi: 10.1007/s12015-014-9580-6.

Bailey A L, Sullivan S M. Efficient encapsulation of DNA plasmids in small neutral liposomes Inducediby ethanol and calcium. Biochim Biophys Acta 2000; 1468:239-52. doi: 10.1016/S0005-2736(00)00264-9.

Balbino T A, Gasperini A A, Oliveira C L, Azzoni A R, Cavalcanti L P, de La Torre L G. Correlation of the physicochemical and structural properties of pDNA/cationic liposome complexes with their in vitro transfection. Langmuir 2012; 28:11535-45.

Barrangou R, Fremaux C, Deveau H, Richards M, Boyaval P, Moineau S, Romero D A, Horvath P. CRISPR provides acquired resistance against viruses in prokaryotes. Science 2007; 315:1709-12.

Bechmann L P, Zahn D, Gieseler R K, Fingas C D, Marquitan G, Jochum C, Gerken G, Friedman S L, Canbay A. Resveratrol amplifies profibrogenic effects of free fatty acids on human hepatic stellate cells. Hepatol Res 2009; 39:601-8.

Bertino G, Demma S, Ardiri A, Proiti M, Mangia A, Gruttadauria S, Toro A, Di Carlo I, Malaguarnera G, Bertino N, Malaguarnera M, Malaguarnera M. The immune system in hepatocellular carcinoma and potential new immunotherapeutic strategies. Biomed Res Int 2015; 2015: 731469. PMID 25893197. Epub 2015 Mar. 29.

Birchall J C, Kellaway I W, Mills S N. Physico-chemical characterisation and transfection efficiency of lipid-based gene delivery complexes. Int J Pharm 1999; 183:195-207.

Boch J. TALEs of genome targeting. Nature Biotech 29; 2011:135-6. doi:10.1038/nbt.1767. PMID 21301438.

Carlson D F, Fahrenkrug S C, Hackett P B. Targeting DNA with fingers and TALENs. Mol Ther Nucleic Acids 2012 Jan. 24; 1:e3. doi: 10.1038/mtna.2011.5. PMID 23344620. CRISPR Data Base: http://crispr.u-psud.fr/crispr/CRISPRdatabase.php (accessed on 2015, 19 Apr.).

Cohen H, Levy R J, Gao J, Fishbein I, Kousaev V, Sosnowski S, Slomkowski S, Golomb G. Sustained delivery and expression of DNA encapsulated in polymeric nanoparticles. Gene Ther 2000; 7:1896-905.

Esvelt K M, Smidler A L, Catteruccia F, Church G M. Concerning RNA-guided gene drives for the alteration of wild populations. elife 2014:e03401. doi: 10.7554/eLife.03401. PMID 25035423.

Felger P L, Ringold G M. Cationic liposome-mediated transfection. Nature 1989; 337:387-88.

Frankel A D, Pabo C O. Cellular uptake of the tat protein from human immunodeficiency virus. Cell 1988; 55:1189-93. PMID 2849510.

Gao J, Chen K, Xie J, Yan Y, Cheng Z, Peng X and Chen X. In vivo tumor-targeted fluorescence imaging using near-infra red non-cadmium quantum dots. Bioconj Chem 2010; 21:604-9.

Gene Silencing NCIB http://www.ncib.nlm.nih.gov/genome/probe/doc/ApplSilencing.shtml (accessed on 2015-04-19)

Gieseler R K, Marquitan G, Hahn M J, Perdon L A, Driessen W H, Sullivan S M, Scolaro M J. D C-SIGN-specific liposomal targeting and selective intracellular compound delivery to human myeloid dendritic cells: implications for HIV disease. Scand J Immunol 2004; 59:415-24. PMID: 15140050.

Gieseler R K, Marquitan G, Hahn M J, Perdon L A, Driessen W H, Sullivan S M, Scolaro M J. D C-SIGN-specific liposomal targeting and selective intracellular compound delivery to human myeloid dendritic cells: implications for HIV disease. Scand J Immunol 2004; 59:415-24. PMID 15140050.

Gieseler R K, Marquitan G, Schlattjan M, Sowa J P, Bechmann L P, Timm J, Roggendorf M, Gerken G, Friedman S L, Canbay A. Hepatocyte apoptotic bodies encasing nonstructural HCV proteins amplify hepatic stellate cell activation: implications for chronic hepatitis C. J Viral Hepat 2011; 18:760-7.

Goodchild J. Chapter I. Therapeutic Oligonucleotides. In: Goodchild J. (ed.). Methods in Molecular Biology: Therapeutic Oligonucleotides. Methods and Protocols. Springer 2011: ISBN 978-1-61779-188-8. Pp. 1-15.

Grunwald T, Ulbert S. Improvement of DNA vaccination by adjuvants and sophisticated delivery devices: vaccine-platforms for the battle against infectious diseases. Clin Exp Vaccine Res 2015; 4:1-10. doi: 10.7774/cevr.2015.4.1.1. Epub 2015 Jan. 30.

Hoving J C, Wilson G J, Brown G D. Signalling C-type lectin receptors, microbial recognition and immunity. Cell Microbiol 2014; 16:185-94. PMID 24330199. doi: 10.1111/cmi.12249. Epub 2014 Jan. 10.

Immordino M L, Doiso F, Cattel L. Stealth liposomes: review of the basic science rationale and clinical applications, existing and potential. Int J Nanomedicine 2006; 1:297-315.

Jabalameli H R, Zahednasab H, Karimi-Moghaddam A, Jabalameli M R. Zinc finger nuclease technology: advances and obstacles in modelling and treating genetic disorders. Gene 2015; 558:1-5. doi: 10.1016/j.gene.2014.12.044. Epub 2014 Dec. 20. PMID 25536166.

James M B, Giogio T D. Nuclear-associated plasmid, but not cell-associated plasmid, is correlated with transgene expression in cultured mammalian cells. Mol Ther 2000; 1:339-46.

Kessler C, Manta V. Specificity of restriction endonucleases and DNA modification methyltransferases: a review. Gene 1990; 92:1-248. doi:10.1016/0378-1119(90)90486-B. PMID 2172084.

Klug A, Rhodes D. Zinc fingers: a novel protein fold for nucleic acid recognition. Cold Spring Harb Symp Quant Biol 1987:52:473-82. PMID: 3135979

Mali P, Esvelt K M, Church G M. Cas9 as a versatile tool for engineering biology. Nature Methods 2013:10:957-63. doi:10.1038/nmeth.2649. PMC 4051438. PMID 24076990.

Marraffini L A, Sontheimer E J. CRISPR interference limits horizontal gene transfer in staphylococci by targeting DNA". Science 2008; 322:1843-1845. doi:10.1126/science.1165771. PMC 2695655. PMID 19095942.

Marraffini L A, Sontheimer E J. CRISPR interference: RNA-directed adaptive immunity in bacteria and archaea. Nat Rev Genet 2010; 11:181-90. doi: 10.1038/nrg2749.

Mbonye U, Karn J. Transcriptional control of HIV latency: cellular signaling pathways, epigenetics, happenstance and the hope for a cure. Virology 2014; 454-455:328-39. PMID 24565118. doi: 10.1016/j.virol.2014.02.008. Epub 2014 Feb. 22.

Mocellin S, Provenzano M. RNA interference: learning gene knock-down from cell physiology. J Translat Med 20014; 2:39. doi:10.1186/1479-5876-2-39. PMID 15555080.

Peer D, Karp J M, Hong S, Farokhazd O C, Margalit R, Langer R. Nanocarrieres as an emerging platform for cancer therapy. Nat Nanotechn 2007; 2:751-60 (2007)

Pérez-Herrero E, Fernández-Medarde A. Advanced targeted therapies in cancer: Drug nanocarriers, the future of chemotherapy. Eur J Pharm Biopharm 2015 Mar. 23. pii: S0939-6411(15)00151-4. doi: 10.1016/j.ejpb.2015.03.018. Epub ahead of print.

Perrie Y, Frederik P M, Gregoriadis G. Liposome-mediated DNA vaccination: the effect of vesicle composition. Vaccine 2001; 19:3301-10.

Pupo E, Padron A, Santana E, Sotolongo J, Quintana D, Dueñas S, Duarte C, de la Rosa M C, Hardy E. Preparation of plasmid DNA-containing liposomes using a high-pressure homogenization-extrusion technique. J Contr Release 2005; 104:379-96. doi: 10.1016/j.jconrel.2005.02.001.

Rajeev K G, Nair J K, Jayaraman M, Charisse K, Taneja N, O'Shea J, Willoughby J L, Yucius K, Nguyen T, Shulga-Morskaya S, Milstein S, Liebow A, Querbes W, Borodovsky A, Fitzgerald K, Maier M A, Manoharan M. Hepatocyte-specific delivery of siRNAs conjugated to novel non-nucleosidic trivalent N-acetylgalactosamine elicits robust gene silencing in vivo. Chembiochem 2015; 16:903-8. doi: 10.1002/cbic.201500023. Epub 2015 Mar. 18.

Roberts R J. Restriction endonucleases. CRC Crit Rev Biochem 1976; 4:123-64

Sarvaiya J, Agrawal Y K. Chitosan as a suitable nanocarrier material for anti-Alzheimer drug delivery. Int J Biol Macromol 2015; 72:454-65. doi: 10.1016/j.ijbiomac.2014.08.052. PMID 25199867. Epub 2014 Sep. 6.

Sharma S. Nanotheranostics in evidence based personalized medicine. Curr Drug Targets 2014; 15:915-30.

Silva A C, Lopes C M, Lobo J M, Amaral M H. Nucleic acids delivery systems: A challenge for pharmaceutical technologists. Curr Drug Metab 2015 Apr. 1. Epub ahead of print.

Siomi H, Siomi M C. On the road to reading the RNA interference code. Nature 2009; 457:396-404. PMID 19158785. doi:10.1038/nature07754.

Sullivan S M, Gieseler R K, Lenzner S, Ruppert J, Gabrysiak T G, Peters J H, Cox G, Richer L, Martin W J, Scolaro M J. Inhibition of human immunodeficiency virus-1 proliferation by liposome-encapsulated sense DNA to the 5' tat splice acceptor site. Antisense Res Dev 1992; 2:187-97. PMID 1490070.

Tachibana R, Harashima H, Ide N, Ukitsu S, Ohta Y, Suzuki N, Kikuchi H, Shinohara Y, Kiwada H. Quantitative analysis of correlation between number of nuclear plasmids and gene expression activity after transfection with cationic liposomes. Pharm Res 2002; 19:377-81.

Ulrich P P, Busch M P, el-Beik T, Shiota J, Vennari J, Shriver K, Vyas G N. Assessment of human immunodeficiency virus expression in cocultures of peripheral blood mononuclear cells from healthy seropositive subjects. J Med Virol 1988; 25:1-10.

Wang A Z, Langer R, Farokhzad O C. Nanoparticles delivery of cancer drugs. Annu Rev Med 2012; 63, 185-98.

Wree A, Broderick L, Canbay A, Hoffman H M, Feldstein A E. From NAFLD to NASH to cirrhosis—new insights into disease mechanisms. Nat Rev Gastroenterol Hepatol 2013; 10:627-36. doi: 10.1038/nrgastro.2013.149. PMID 23958599. Epub 2013 Aug. 20.

Xenopoulos A, Pattnaik P. Production and purification of plasmid DNA vaccines: is there scope for further innovation? Expert Rev Vaccines 2014; 13:1537-51. doi: 10.1586/14760584.2014.968556. Epub 2014 Oct. 13.

The invention claimed is:

1. A method for treating a patient suffering from malignant diseases, autoimmune diseases, inherited disorders, or metabolic disorders of the liver with a lipid-based nanocarrier selected from the group consisting of a liposome, a lipoplex, or a micelle, wherein the nanocarrier specifically targets hepatocytes by administering the nanocarrier to the patient, said nanocarrier comprising both of:

a tool for gene therapy as a therapeutic payload selected from an artificially engineered restriction enzyme or a CRISPR/Cas system, or a plasmid specifically encoding the artificially engineered restriction enzyme or the CRISPR/Cas system, wherein the artificially engineered restriction enzyme is a zinc finger nuclease (ZFN) or a transcription activator-like effector nuclease (TALEN) and the plasmid expresses the artificially engineered restriction enzyme or the CRISPR/Cas system either upon integration into the patient's cell genome or extra-chromosomally and a targeting anchor comprising a lipid anchor moiety and a hepatocyte-targeting moiety, wherein a spacer moiety is inserted between the lipid anchor moiety and the hepatocyte-targeting moiety, wherein the spacer moiety is 3,4,5-trihydroxy-6-(hydroxymethyl)tetrahydro-2H-pyran-2-yl)thioureido) butyl)carbamate, N-hydroxysuccinimide (NHS), 1,2-Distearoyl-sn-glycero-3-phosphoethanolamin-N-[poly (ethylenglycol)-2000]-N-Hydroxysuccinimid (DSPE-PEG-NHS), ε-aminocaproic acid, a polyaldehyde, a polyolefin, a polyethylene oxide, a poly-ω-alkenoic acid ester or a polyalkyl methacrylate, wherein the hepatocyte-targeting moiety is cholesten-5-yloxy-N-(4-((1-imino-2-ß-D-thio[CHO*]ethyl)amino)butyl)formamide, wherein CHO* stands for D,L-galactose, D-galactose, L-galactose and/or N-acetylgalactosamine, wherein said targeting anchor is covalently linked to the nanocarrier at an outer surface of the nanocarrier and binds to a receptor molecule expressed on the surface of the hepatocytes via the hepatocyte-targeting moiety.

2. The method according to claim 1, wherein the nanocarrier is administered via an intravenous, a subcutaneous, an intradermal, an intraperitoneal, a parenteral, a route by infusion via the hepatic artery, or an intranasal route.

* * * * *